United States Patent
Keum et al.

(10) Patent No.: US 11,969,028 B2
(45) Date of Patent: Apr. 30, 2024

(54) BRASSIERE FOR RADIATION THERAPY

(71) Applicant: Industry-Academic Cooperation Foundation, Yonsei University, Seoul (KR)

(72) Inventors: Ki Chang Keum, Seoul (KR); Seung Kwon Ahn, Seoul (KR); Sam Ju Cho, Seoul (KR); Yong Bae Kim, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 261 days.

(21) Appl. No.: 17/297,969

(22) PCT Filed: Aug. 19, 2020

(86) PCT No.: PCT/KR2020/010870
§ 371 (c)(1),
(2) Date: May 27, 2021

(87) PCT Pub. No.: WO2021/075695
PCT Pub. Date: Apr. 22, 2021

(65) Prior Publication Data
US 2022/0087329 A1 Mar. 24, 2022

(30) Foreign Application Priority Data

Oct. 14, 2019 (KR) .................. 10-2019-0126894
Aug. 6, 2020 (KR) .................. 10-2020-0098537

(51) Int. Cl.
*A41C 3/00* (2006.01)
(52) U.S. Cl.
CPC .......... *A41C 3/0064* (2013.01); *A41C 3/0021* (2013.01)

(58) Field of Classification Search
CPC .... A61N 2005/1092; A61N 2005/1094; A61N 2005/1097; A61N 5/10; A61N 5/1001
See application file for complete search history.

(56) References Cited

U.S. PATENT DOCUMENTS

| 706,044 | A | * | 8/1902 | Gillet | .................. F16G 1/28 |
| | | | | | 156/76 |
| 1,962,314 | A | * | 6/1934 | Lytton | .................. A41C 3/00 |
| | | | | | D2/708 |

(Continued)

FOREIGN PATENT DOCUMENTS

| BE | 1019613 A5 | 9/2012 |
| CH | 279519 A | 11/1951 |

(Continued)

OTHER PUBLICATIONS

Notice of Allowance, Chinese Patent Application No. CN202080006149. 4, dated Sep. 5, 2022, 5 pages.

(Continued)

*Primary Examiner* — Jocelyn Bravo
(74) *Attorney, Agent, or Firm* — Berkeley Law & Technology Group, LLP

(57) ABSTRACT

A brassiere for radiation therapy is disclosed. The brassiere for radiation therapy according to an embodiment of the present disclosure includes a pair of cups configured to cover breasts of a patient; a coupling member positioned between the pair of cups and configured to couple the pair of cups to each other; back bands configured to be in close contact with a back of the patient; and side compression bands, the side compression bands having one ends coupled to the pair of cups at the coupling member, respectively, and the other ends detachably coupled to the back bands, respectively, wherein positions of the breasts of the patient are changed by adjusting positions on the back bands to which the other ends of side compression bands are coupled.

(Continued)

According to the embodiment of the present disclosure, it is possible to provide a brassiere for radiation therapy that is capable of compressing the breasts of the patient enough to flatten irregularities of breast skin tissue without excessively compressing a chest of the patient, and of isolating a contra-lateral intact breast to prevent a radiation dose from being transmitted to the contra-lateral intact breast.

6 Claims, 18 Drawing Sheets

(56) References Cited

U.S. PATENT DOCUMENTS

| | | | |
|---|---|---|---|
| 2,284,382 A * | 5/1942 | Elberfeld | A41C 3/00 D2/708 |
| 2,390,142 A | 12/1945 | Witkower | |
| 2,773,261 A * | 12/1956 | Schaumer | A41C 3/00 450/86 |
| 2,782,416 A * | 2/1957 | Ginsburg | A41C 3/148 450/55 |
| 3,507,285 A * | 4/1970 | Williams | A41C 3/0064 450/122 |
| 4,257,412 A | 3/1981 | Guttentag | |
| 4,802,469 A | 2/1989 | Gollestani | |
| 5,098,331 A * | 3/1992 | Corrado | A61F 13/145 450/58 |
| 5,660,577 A * | 8/1997 | Modena | A41C 3/00 450/86 |
| 5,968,003 A * | 10/1999 | Sisson | A61F 13/145 602/53 |
| 8,932,103 B2 * | 1/2015 | Hansen | A41C 3/0028 450/86 |
| 9,192,197 B2 * | 11/2015 | Reinhard | A41C 3/02 |
| 9,756,880 B1 * | 9/2017 | Malik | A41C 3/04 |
| 10,136,681 B1 * | 11/2018 | Malik | A41C 3/0064 |
| 2002/0121273 A1 | 9/2002 | Nyilas | |
| 2004/0147989 A1 | 7/2004 | Terakita et al. | |
| 2004/0219864 A1 | 11/2004 | Kermode et al. | |
| 2005/0130558 A1 | 6/2005 | Wooten | |
| 2012/0244782 A1 * | 9/2012 | Pundyk | A41C 3/0057 450/70 |
| 2013/0065486 A1 * | 3/2013 | Hansen | A41C 3/0064 450/59 |
| 2013/0084776 A1 | 4/2013 | Walsh | |
| 2013/0316616 A1 | 11/2013 | Thompson | |
| 2015/0073254 A1 * | 3/2015 | Talant | A61B 6/4417 600/407 |
| 2015/0099420 A1 * | 4/2015 | Reinhard | A41C 3/02 450/58 |
| 2015/0264982 A1 | 9/2015 | Randall et al. | |
| 2016/0228288 A1 | 8/2016 | Nelson et al. | |
| 2016/0249688 A1 | 9/2016 | Ibey et al. | |
| 2018/0229052 A1 | 8/2018 | Lu et al. | |
| 2020/0323279 A1 * | 10/2020 | Castillo Piedra | A41C 3/0057 |
| 2022/0304394 A1 * | 9/2022 | Castillo Piedra | A41C 3/0021 |

FOREIGN PATENT DOCUMENTS

| | | |
|---|---|---|
| CN | 2171217 Y | 7/1994 |
| CN | 2593582 Y | 12/2003 |
| CN | 2927722 Y | 8/2007 |
| CN | 201700413 U | 1/2011 |
| CN | 202722513 U | 2/2013 |
| CN | 103285527 A | 9/2013 |
| CN | 103476281 A | 12/2013 |
| CN | 103960832 A | 8/2014 |
| CN | 106213596 A | 12/2016 |
| CN | 205831980 U | 12/2016 |
| DE | 202008006846 U1 | 7/2008 |
| DE | 202015106741 U1 | 12/2015 |
| FR | 381806 A | 1/1908 |
| FR | 2967014 A1 | 5/2012 |
| JP | S6086342 U | 6/1985 |
| JP | H10327910 A | 12/1998 |
| JP | 2017225652 A | 12/2017 |
| JP | 2019007121 A | 1/2019 |
| KR | 1020120019887 | 3/2012 |
| KR | 101694851 B1 | 1/2017 |
| KR | 200483243 B1 | 4/2017 |
| KR | 101888510 B1 | 8/2018 |
| WO | 2008144818 A1 | 12/2008 |
| WO | 2017220997 A1 | 12/2017 |

OTHER PUBLICATIONS

First Office Action, App. No. CN202080006149.4, dated Jun. 1, 2022, 22 Pages.

Written Decision on Registration, App. No. KR10-2020-0098537, dated Oct. 11, 2022, 6 pages.

* cited by examiner

BRASSIERE FOR RADIATION THERAPY

TECHNICAL FIELD

The present disclosure relates to a brassiere for radiation therapy, and more particularly, to a brassiere for radiation therapy capable of isolating an intact breast of a patient from a breast having a tumor and of preventing the intact breast from being visually exposed, when performing radiation therapy on the breast having the tumor.

BACKGROUND ART

Examples of methods for breast cancer therapy include, for example, surgical mastectomy and radiation therapy, chemotherapy, and hormone therapy, and there are differences in therapy methods depending on the stage. At the early stage, radiation therapy is performed along with a lumpectomy.

When planning radiation therapy for breast cancer, for example, a radiation dose irradiated to a contra-lateral breast and the lungs inside the chest wall, posture reproducibility of the patient, and fixation effect of the patient should be considered as important factors.

In order to irradiate an appropriate radiation dose to, for example, the breasts, chest wall, and loco-regional lymphatics when performing radiation therapy, it is necessary to use a patient-fixing device to ensure correct posture reproducibility of the patient during radiation therapy.

Variables exist in the planning of commonly used two-dimensional radiation therapy. That is, for example, it is necessary to take into account an unclear delineation between a tumor and sensitive tissue, and resulting problems regarding a beam shape and the delineation, biological considerations, a dose heterogeneity for the tumor, and posture and movement of the patient.

Korean Patent Registration No. 1888510 (hereinafter referred to as 'Related Art 1') discloses a brassiere for radiation therapy. The brassiere for radiation therapy disclosed in Related Art 1 includes two breast cups, a medial window disposed between the two breast cups and being visually transparent, two shoulder straps for supporting the two breast cups, and a back band coupled to the two shoulder straps and the two breast cups.

Excessively large or sagging breasts within the breast cups cause severe irregularities of the enlarged skin tissue thereof. However, the brassiere for radiation therapy disclosed in Related Art 1 has a disadvantage in that since the breast cups are made of a thin fiber, it is difficult to compress and completely flatten the severe irregularity sites of the breasts, due to elasticity of the thin fiber.

In addition, the brassiere for radiation therapy disclosed in Related Art 1 has a disadvantage in that although detachable coupling between the breast cups, the shoulder straps, and the back band forms tension to support the breast cups, since an adjustable length range of the shoulder straps and the back band is relatively small, it is difficult to properly compress the chest of a patient having a small chest circumference. On the contrary, there is also a disadvantage in that the brassiere excessively compresses the chest of a patient having a large chest circumference.

Therefore, the brassiere for radiation therapy disclosed in Related Art 1 has a disadvantage in that in order to stably support the breasts of patients having different breast sizes and chest circumferences, the brassiere for each patient should be individually manufactured based on a result of measuring the breast size and chest circumference of each patient. Cancer therapy is an uncomfortable and difficult process for patients. Patients may easily experience weight loss or gain while undergoing radiation therapy. Accordingly, there is a need for a method to stably support the breasts of the patient with an appropriate compression force despite a size change of the breasts and chest circumference resulting from weight change.

On the other hand, total mastectomy is an operation in which the entire breast is mastectomized during breast cancer therapy. A total mastectomy is considered when extensive spread of the cancer or recurrence of the cancer due to an excessively advanced stage is expected.

In this regard, Korean Patent Registration No. 1694851 (hereinafter referred to as 'Related Art 2') discloses a brassiere for compressing breasts after a mastectomy. The brassiere for compressing the breasts after the mastectomy, disclosed in Related Art 2, includes a pair of caps having a cap for covering a mastectomized breast after the mastectomy and a cap for covering an intact breast, a supporting band for fixing the pair of caps on the upper body of the patient, and a pair of shoulder straps for fixing the pair of caps on both shoulders, respectively.

The supporting band includes a back supporting band for elastically compressing the back of the patient and extending toward the armpit on the side of the mastectomized breast, a chest supporting band having one end coupled to the back supporting band and elastically compressing the chest and the other end extending toward the armpit on the side of the mastectomized breast, and a band coupling part for detachably coupling the back supporting band to the chest supporting band.

The band coupling part has an adjustable coupling length to adjust a force of the chest supporting band and the cap for compressing the mastectomized breast. Therefore, the brassiere for compressing the breasts after the mastectomy, disclosed in Related Art 2, has an advantage in that it may be used selectively depending on the position of the mastectomized breast and thus compress the mastectomized breast more effectively, resulting in quick healing of a resected site of the mastectomized breast.

However, although the tumor is completely removed through the mastectomy, the tumor may recur in the remaining breast tissue. In particular, a malignant tumor may recur in skin around the breast, chest wall, axillary, and lymph nodes in the neck, and may spread throughout the body along blood vessels or lymphatic vessels and cause distant metastasis in sites such as bones, lungs, liver, and brain.

Accordingly, when there is a high probability of recurrence of the malignant tumor in the chest wall or its surrounding lymph nodes even after total mastectomy, it is possible to reduce the probability of recurrence of the malignant tumor through additional radiation therapy compared to when there is no additional radiation therapy, and to extend the lifespan of the patient.

It has been reported that patients who have undergone total mastectomy for cancer removal experience social and psychological problems such as losing their identity as a woman. Patients who have undergone total mastectomy will undergo radiation therapy with their tops removed. Therefore, the intact breast of the patient is exposed during radiation therapy, and this exposure of the intact breast causes negative effects on psychology of the patient, such as anxiety and shame.

However, the brassiere for compressing the breasts after the mastectomy, disclosed in Related Art 2, only serves to compress the mastectomized breast so as to enable the mastectomized breast to heal quickly. Therefore, there is a need for development of a brassiere that is capable of assisting quick healing of the mastectomized breast by compressing the mastectomized breast in normal situations, and of easily removing the cup of the breast that has undergone total mastectomy while preventing the intact breast from being exposed during radiation therapy.

DISCLOSURE OF INVENTION

Technical Problem

The present disclosure is directed to providing a brassiere for radiation therapy capable of compressing breasts of a patient enough to flatten irregularities of breast skin tissue without excessively compressing a chest of the patient, and of stably supporting the breasts with an appropriate compression force despite a size change of the breasts and chest circumference or a size change of only one breast resulting from a weight change of the patient.

In addition, the present disclosure is further directed to providing a brassiere for radiation therapy capable of assisting quick healing of a mastectomized breast of a patient by compressing the mastectomized breast in normal situations, and of preventing an intact breast from being exposed during radiation therapy.

Solution to Problem

A brassiere for radiation therapy according to an embodiment of the present disclosure includes a pair of cups configured to cover breasts of a patient; a coupling member positioned between the pair of cups and configured to couple the pair of cups to each other; back bands configured to be in close contact with a back of the patient; and side compression bands, the side compression bands having one ends coupled to the pair of cups at the coupling member, respectively, and the other ends detachably coupled to the back bands, respectively, wherein positions of the breasts are changed by adjusting the positions on the back bands to which the other ends of the side compression bands are coupled.

The pair of cups, the coupling member, and the side compression bands may be made of an air equivalent material woven in a mesh shape.

The brassiere for radiation therapy may further include side bands configured to be in close contact with both flanks of the patient, respectively, and to couple the pair of cups to the back bands, respectively.

The brassiere for radiation therapy may further include shoulder bands, the shoulder bands having one ends coupled to the pair of cups at the lower sides of the breasts of the patient, respectively, and the other ends detachably coupled to the back bands, respectively, and the positions of the breasts of the patient are changed by adjusting the positions on the back bands to which the other ends of the shoulder bands are coupled.

The shoulder bands may be made of the air equivalent material woven in the mesh shape.

The middle portions of the side compression bands may be configured to be in close contact with both flanks of the patient, and the middle portions of the shoulder bands may be configured to be in close contact with both shoulders of the patient.

The side compression bands may be configured to be coupled to the back bands by a hook or Velcro, and the back bands may include a first back band and a second back band, the first back band and the second back band being coupled to each other by the hook or Velcro.

The pair of cups may include a first cup configured to cover one breast of the patient; and a second cup configured to cover a mastectomized breast of the patient. The brassiere for radiation therapy may further include a first side band configured to extend from the first cup and to be detachably coupled to one of the back bands; a second side band configured to extend from the second cup and to be detachably coupled to one of the back bands; and at least one coupling band, the at least one coupling band having one end extending from the first cup or the second cup and the other end detachably coupled to one of the back bands, wherein the at least one coupling band may couple the first cup and one of the back bands to each other at the opposite side of the first side band even upon removal of the second cup and the second side band.

The first cup, the second cup, the coupling member, the first side band, the second side band, and the at least one coupling band may be made of the air equivalent material.

The brassiere for radiation therapy may further include a first shoulder band, the first shoulder band having one end coupled to the first cup and the other end detachably coupled to one of the back bands; and a second shoulder band, the second shoulder band having one end coupled to the second cup and the other end detachably coupled to the other of the back bands.

The at least one coupling band may be configured to be detachably coupled to the first cup or the second cup.

The at least one coupling band may include a first coupling band configured to be coupled to the first cup; and a second coupling band configured to be coupled to the second cup, wherein the first coupling band may couple the first cup and one of the back bands to each other at the opposite side of the first side band even upon removal of the second cup and the second side band.

The first shoulder band and the first coupling band may be configured to be detachably coupled to one of the back bands by a snap button.

The snap button may include female snaps provided on the back bands; a first male snap provided on the first shoulder band; and a second male snap provided on the first coupling band, wherein upon coupling the second male snap to one of the female snaps, the first male snap may be interposed between the one of the female snaps and the second male snap.

The female snaps may include a housing configured to be coupled to the back bands; and flexural deformable members installed in the housing. The first male snap may include a first body configured to be coupled to the first shoulder band; a first extending portion configured to extend from the first body; and a first expanding portion formed at an end of the first extending portion and configured to be caught by the flexural deformable members.

The second male snap may include a second body configured to be coupled to the second shoulder band; second extending portions configured to extend from the second body; and second expanding portions formed at ends of the second extending portions and configured to be caught by the flexural deformable members, and the first expanding portion and the second expanding portions may be caught by the flexural deformable members at opposite sides with respect to the flexural deformable members.

The first extending portion and the first expanding portion may be spaced apart from deformation sections of the flexural deformable members by the second expanding portions so as not to restrain elastic flexural deformation of the flexural deformable members by the second expanding portions, and the second extending portions and the second expanding portions may be positioned within the deformation sections of the flexural deformable members by the first expanding portion so as to restrain elastic flexural deformation of the flexural deformable members by the first expanding portion.

The second extending portions may include a second extending portion A and a second extending portion B, the second expanding portions may include a second expanding portion A formed at the second extending portion A and a second expanding portion B formed at the second extending portion B, and the second expanding portion A and the second expanding portion B may be caught by the flexural deformable members at opposite sides with respect to the first expanding portion.

The flexural deformable members may include a first flexural deformable member configured to catch the second expanding portion A; and a second flexural deformable member configured to catch the second expanding portion B, and the first flexural deformable member and the second flexural deformable member may be deformed symmetrically with each other.

Advantageous Effects of Invention

According to embodiments of the present disclosure, it is possible to provide a brassiere for radiation therapy capable of compressing breasts of the patient enough to flatten irregularities of breast skin tissue without excessively compressing a chest of the patient, and of isolating a contra-lateral intact breast to prevent a radiation dose from being transmitted to the contra-lateral intact breast, by adjusting force of the side compression bands for compressing the breasts while being on the pair of cups, through adjusting the positions on the back bands to which the other ends of the side compression bands are coupled.

In addition, according to the embodiments of the present disclosure, it is possible to provide a brassiere for radiation therapy capable of stably supporting the breasts of a patient with an appropriate compression force despite a size change of the breasts and chest circumference or a size change of only one breast resulting from a weight change of the patient, and of reducing transmission of a radiation dose to the lungs and the heart positioned in the direction of the tumor by moving lower breast tissues in the direction of the nipples and reducing a transmission range of the radiation dose, by adjusting force of the shoulder bands for compressing the breasts while being on the pair of cups, through adjusting the positions on the back bands to which the other ends of the shoulder bands are coupled.

In addition, according to the embodiment of the present disclosure, it is possible to provide a brassiere for radiation therapy capable of assisting quick healing of the mastectomized breast by compressing the mastectomized breast in normal situations, and of easily removing the cup covering the breast that has undergone total mastectomy while preventing the intact breast from being exposed during radiation therapy, by coupling the first cup and one of the back bands to each other through one of the coupling bands at the opposite side of the second side band when removing the second cup and the second side band.

In addition, according to the embodiments of the present disclosure, it is possible to provide a brassiere for radiation therapy capable of preventing the intact breast from being exposed even if some of coupling parts of the brassiere are released accidentally or by an external force during radiation therapy, by positioning the second extending portions and the second expanding portions within the deformation sections of the flexural deformable members by the first expanding portion so as to restrain elastic flexural deformation of the flexural deformable members by the first expanding portion.

DESCRIPTION OF EMBODIMENTS

Hereinafter, preferred embodiments of the present disclosure will be described in detail with reference to the accompanying drawings. However, the detailed description of known technologies and configurations will be omitted in order to avoid unnecessarily obscuring the subject matter of the present disclosure.

A brassiere for radiation therapy according to the embodiments of the present disclosure is configured to compress breasts of a patient enough to flatten irregularities of breast skin tissue without excessively compressing a chest of the patient, and to stably support the breasts with an appropriate compression force despite a size change of the breasts and chest circumference or a size change of only one breast resulting from a weight change of the patient.

In addition, the brassiere for radiation therapy is also configured to isolate a contra-lateral intact breast to prevent a radiation dose from being transmitted to the contra-lateral intact breast, and to reduce transmission of the radiation dose to the lungs and the heart positioned in the direction of the tumor by moving lower breast tissues in the direction of the nipples and reducing a transmission range of the radiation dose.

In addition, the brassiere for radiation therapy is also configured to assist quick healing of a mastectomized breast by compressing the mastectomized breast in normal situations, and to easily remove a cup covering the breast that has undergone total mastectomy while preventing the intact breast from being exposed during radiation therapy.

BEST MODE FOR CARRYING OUT THE INVENTION

First Embodiment

Figure 1:
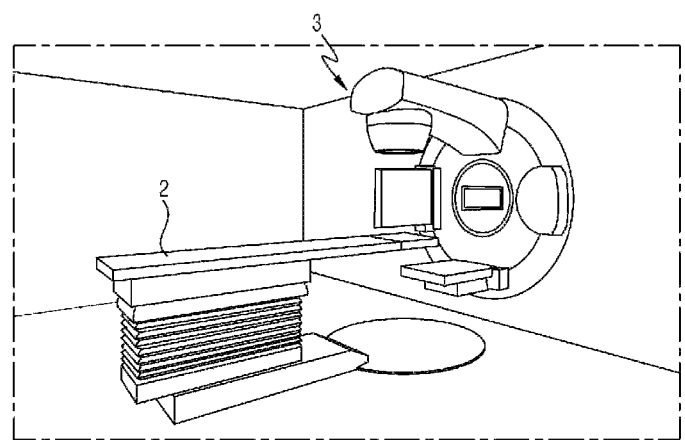
FIG. 1 is a view illustrating a device for radiation therapy and a couch.
Figure 2:
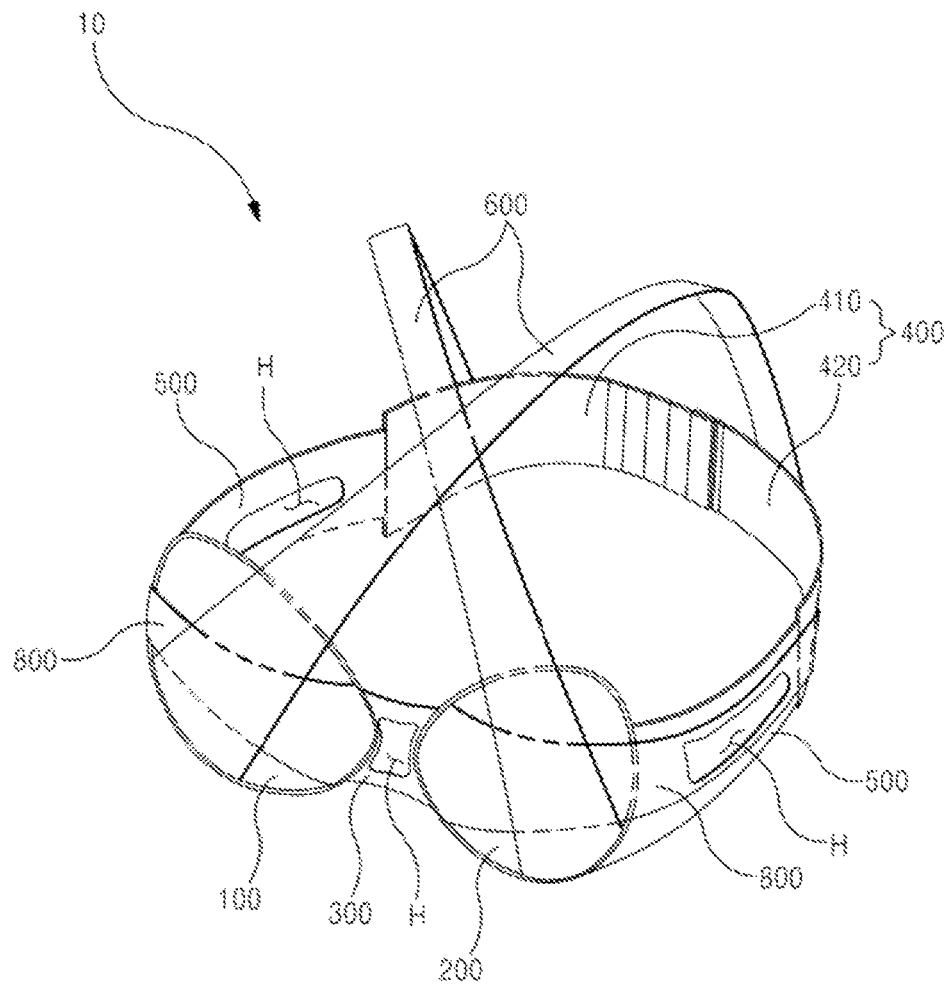
FIG. 2 is a front perspective view of a brassiere for radiation therapy according to a first embodiment of the present disclosure.

FIG. 1 is a view illustrating a device for radiation therapy and a couch, and FIG. 2 is a front perspective view of a brassiere for radiation therapy according to a first embodiment of the present disclosure.

Figure 3:
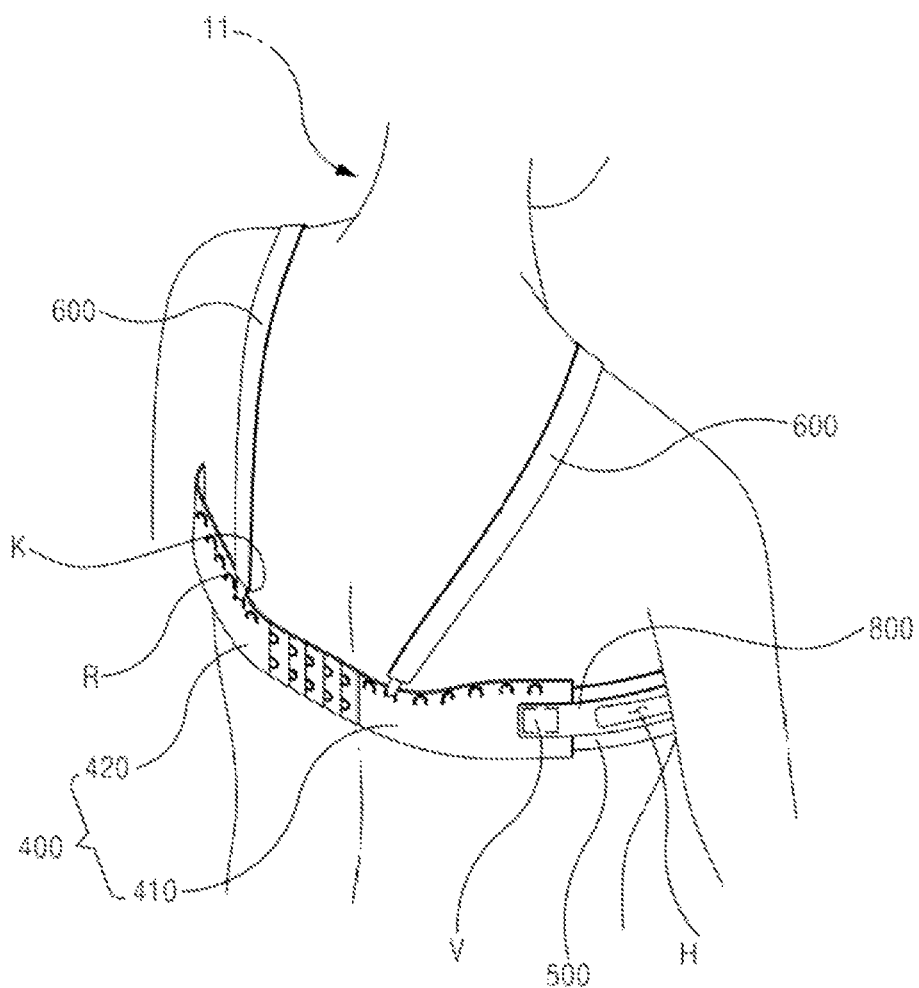
FIG. 3 is a rear perspective view illustrating a state in which the brassiere for radiation therapy of FIG. 2 is worn.
Figure 4:
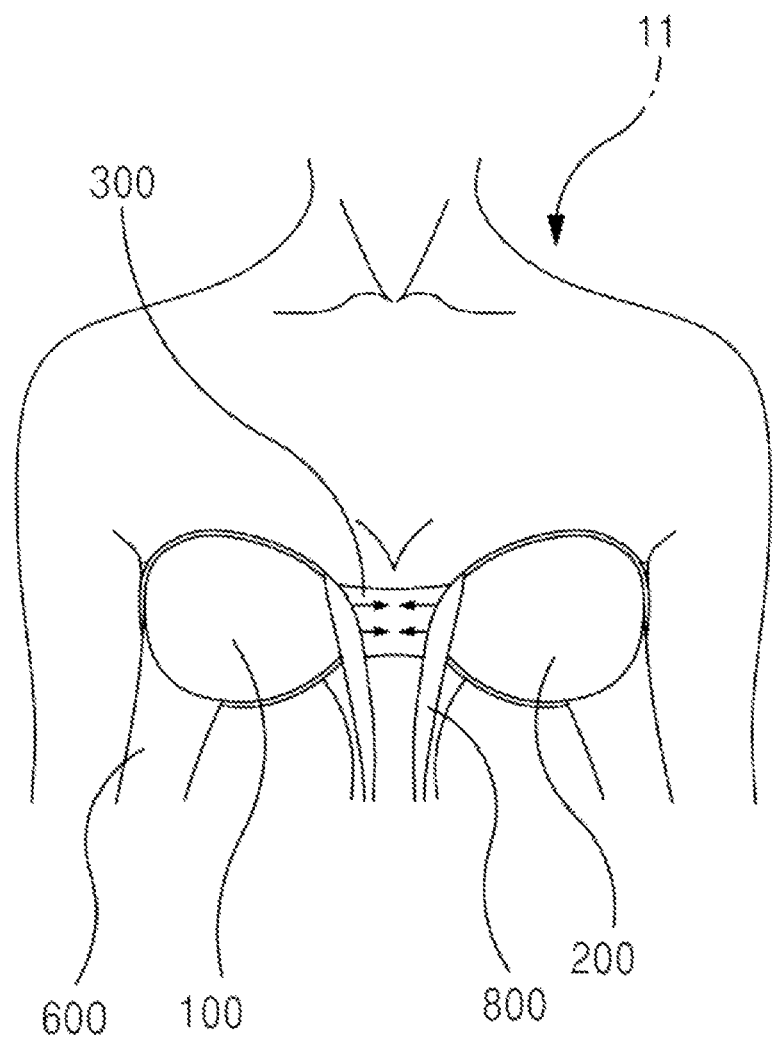
FIGS. 4 to 6 are views illustrating a process of putting on the brassiere for radiation therapy of FIG. 2.
Figure 5:
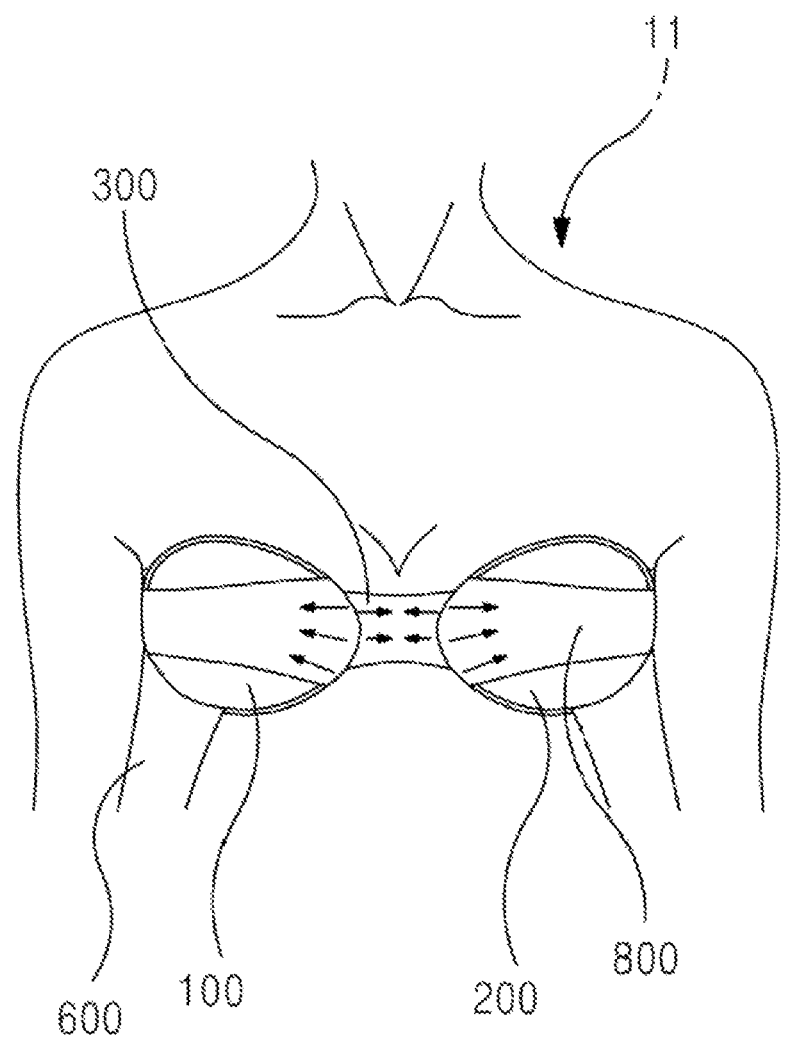
Figure 6:
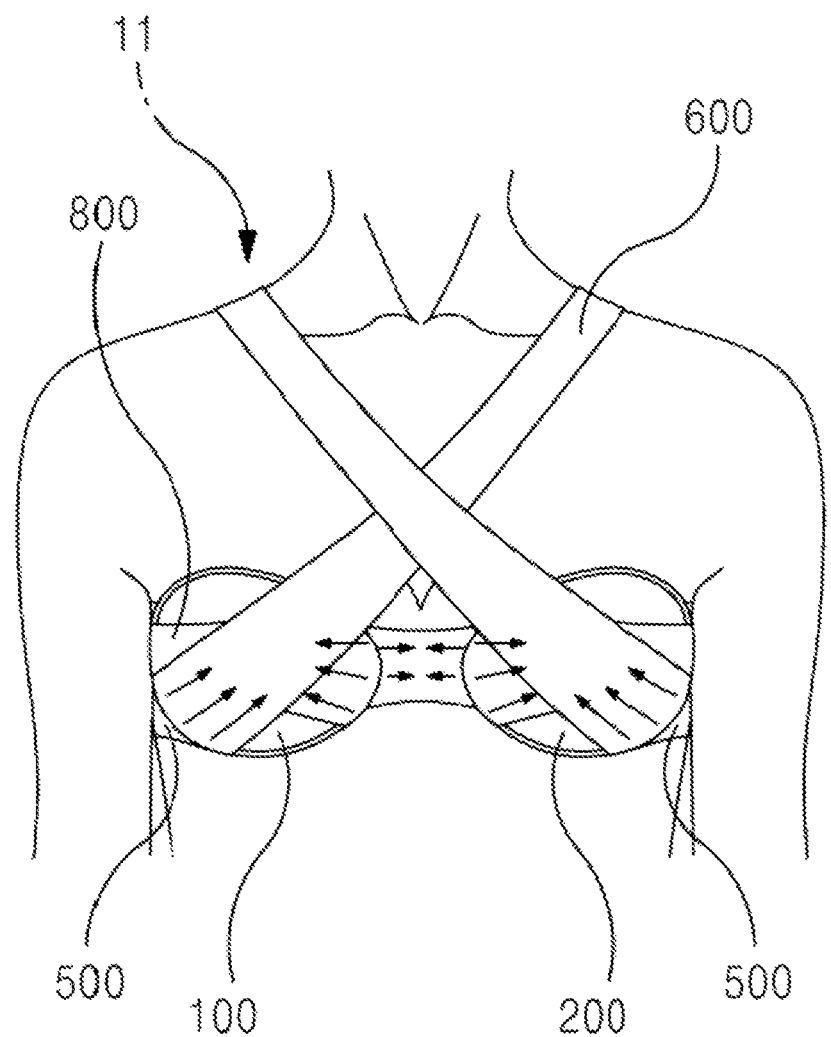

FIG. 3 is a rear perspective view illustrating a state in which the brassiere for radiation therapy of FIG. 2 is worn, and FIGS. 4 to 6 are views illustrating a process of putting on the brassiere for radiation therapy of FIG. 2.

Figure 7:
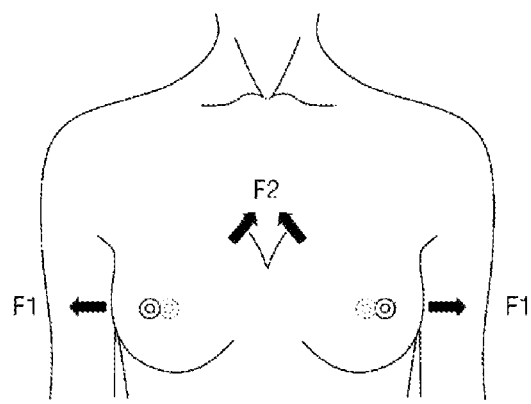
FIGS. 7 and 8 are views illustrating movement of breasts by the brassiere for radiation therapy of FIG. 2.
Figure 8:
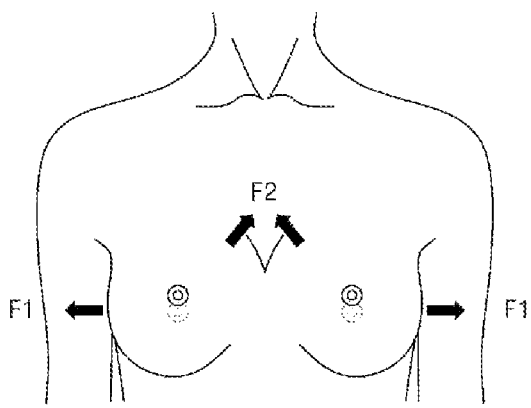

FIGS. 7 and 8 are views illustrating movement of breasts by the brassiere for radiation therapy of FIG. 2.

As illustrated in FIG. 1, when performing radiation therapy on breasts of a patient (not shown), the patient lies on a couch 2, and radiation generated by a device for radiation therapy 3 is irradiated to the lesion sites of the breasts.

As illustrated in FIGS. 2 to 6, a brassiere for radiation therapy 10 according to the first embodiment of the present disclosure is configured to, while radiation therapy is performed on the breasts of the patient 11, move the breasts and keep the positions of the moved breasts unchanged, and includes a pair of cups 100 and 200, a coupling member 300, a pair of back bands 400, a pair of side bands 500, a pair of side compression bands 800, and pair of shoulder bands 600.

As illustrated in FIG. 2, the pair of cups 100 and 200 are configured to cover the breasts of the patient 11, respectively, and include a first cup 100 and a second cup 200.

The first cup 100 is configured to cover a right breast of the patient 11. The second cup 200 is configured to cover a left breast of the patient 11. The first cup 100 and the second cup 200 are configured to be in close contact with the breasts by the coupling member 300, the pair of side bands 500, the pair of side compression bands 800, and the pair of shoulder bands 600.

The first cup 100 and the second cup 200 are coupled to each other by the coupling member 300. The coupling member 300 is positioned between the first cup 100 and the second cup 200, and is configured to couple the first cup 100 and the second cup 200 to each other.

Both ends of the coupling member 300 may be coupled to the first cup 100 and the second cup 200, respectively. Both ends of the coupling member 300 may be coupled to the edges of the pair of cups 100 and 200, respectively, through sewing, bonding, or heat fusion. Alternatively, the first cup 100, the second cup 200, and the coupling member 300 may be integrally manufactured.

The first cup 100 and the second cup 200 may be formed to have a symmetrical structure with respect to the coupling member 300. That is, the first cup 100 and the second cup 200 may be formed to have the same structure in addition to the symmetrical structure. Hereinafter, it should be understood that the pair of cups 100 and 200 refer to the first cup 100 and the second cup 200.

As illustrated in FIG. 2, a hole H may be formed in the middle portion of the coupling member 300, so that a set-up line on the skin of the patient may be seen through the hole H.

The pair of cups 100 and 200 and the coupling member 300 are made of an air equivalent material. The air equivalent material refers to a material that has the same effective atomic number as air and exhibits the same ionization effect for radiation as air. Examples of air equivalent materials include graphite, paper, and certain plastics.

The pair of cups 100 and 200 may be made of carbon fiber woven in a mesh shape. When made of the carbon fiber, since the pair of cups 100 and 200 exhibit the same ionization effect for radiation as air, the pair of cups 100 and 200 do not affect a radiation dose irradiated to the lesion sites of the breasts. When the pair of cups 100 and 200 are woven in the mesh shape, deformation of the pair of cups 100 and 200 is facilitated by applying an external force to the pair of cups 100 and 200.

By changing a direction and intensity of the applied external force according to a size and shape of the breasts, an area and shape of the pair of cups 100 and 200 may be changed. The external force is applied to the pair of cups 100 and 200 by the coupling member 300, the pair of side bands 500, the pair of side compression bands 800, and the pair of shoulder bands 600.

As illustrated in FIGS. 2 and 3, the pair of back bands 400 are configured to be in close contact with the back of the patient 11, and include a first back band 410 and a second back band 420.

The first back band 410 and the second back band 420 are detachably coupled to each other by a hook K or Velcro V. The first back band 410 and the second back band 420 are formed in a strap shape, respectively. The first back band 410 and the second back band 420 are made of a fibrous material having elasticity. The pair of back bands 400 may also be made of the carbon fiber.

As illustrated in FIGS. 2 and 3, the pair of side bands 500 are provided on both flanks of the patient 11, respectively, and couple the pair of cups 100 and 200 to the pair of back bands 400, respectively.

That is, one of the pair of side bands 500 is provided on one flank of the patient 11, and couples the first cup 100 and the first back band 410 to each other. In addition, the other of the pair of side bands 500 is provided on the other flank of the patient 11, and couples the second cup 200 and the second back band 42 to each other. The pair of side bands 500 are configured to be in close contact with both flanks of the patient 11, respectively.

One ends of the pair of side bands 500 may be coupled to the first cup 100 and the second cup 200, respectively, at opposite sides of the first cup 100 and the second cup 200 to the coupling member 300. The one ends of the pair of side bands 500 may be coupled to the edges of the pair of cups 100 and 200, respectively, through sewing, bonding, or heat fusion.

Alternatively, the first cup 100 and the second cup 200 may be integrally manufactured with the pair of side bands 500. The pair of side bands 500 may be made of the air equivalent material. The other ends of the pair of side bands 500 are coupled to the first back band 410 and the second back band 420, respectively.

As illustrated in FIG. 4, by covering the breasts of the patient 11 with the first cup 100 and the second cup 200 and coupling the first back band 410 and the second back band 420 to each other at the back of the patient 11, a state in which the breasts of the patient 11 are covered with the first cup 100 and the second cup 200 can be maintained through the elasticity of the pair of cups 100 and 200, the coupling member 300, and the pair of side bands 500.

As illustrated in FIGS. 2 and 3, the pair of side compression bands 800 are configured to compress the breasts of the patient 11 while being on the pair of cups 100 and 200.

One ends of the pair of side compression bands 800 are coupled to the pair of cups 100 and 200 at the coupling member 300, respectively. The one ends of the pair of side compression bands 800 may be coupled to the edges of the pair of cups 100 and 200, respectively, through sewing, bonding, or heat fusion. Alternatively, the pair of cups 100 and 200 and the pair of side compression bands 800 may be integrally manufactured. The pair of side compression bands 800 may be made of the air equivalent material.

The pair of side compression bands 800 may be made of the carbon fiber woven in the mesh shape. When made of the carbon fiber, since the pair of side compression bands 800 exhibit the same ionization effect for radiation as air, the pair of side compression bands 800 do not affect the radiation dose irradiated to the lesion sites of the breasts.

When the pair of side compression bands 800 are woven in the mesh shape, deformation of the pair of side compression bands 800 is facilitated by applying an external force to the pair of side compression bands 800. As a result, it is possible to easily adjust the compression force of the pair of side compression bands 800 by the external force.

As illustrated in FIG. 3, the other ends of the pair of side compression bands 800 are detachably coupled to the pair of back bands 400, respectively. The pair of side compression bands 800 and the pair of back bands 400 are detachably coupled to each other by the hook K or Velcro V. The middle portions of the pair of side compression bands 800 are configured to be in close contact with both flanks of the patient 11.

The pair of side compression bands 800 are formed in a long strap shape as a whole. The pair of side compression bands 800 are formed to have a wider width toward the coupling member 300. As a result, the pair of side compression bands 800 are formed to cover the breasts while being on the pair of cups 100 and 200.

As illustrated in FIG. 5, when the other ends of the pair of side compression bands 800 are coupled to the pair of back bands 400, respectively, the pair of side compression bands 800 form elasticity for pulling the pair of cups 100 and 200 away from the coupling member 300 while covering the breasts. The pair of side compression bands 800 compress the breasts of the patient 11 by maintaining the tensile force applied thereto, and thus isolate the contra-lateral intact breast from the breast having the tumor.

By adjusting the positions on the pair of back bands 400 to which the other ends of the pair of side compression bands 800 are coupled, it is possible to adjust a force of the pair of side compression bands 800 for compressing the breasts of the patient 11 while being on the pair of cups 100 and 200. As a result, it is possible to compress the breasts of the patient 11 enough to flatten irregularities of breast skin tissue without excessively compressing the chest of the patient 11.

In addition, it is possible to stably support the breasts with an appropriate compression force despite a size change of the breasts and chest circumference or a size change of only one breast resulting from a weight change of the patient 11.

As illustrated in FIG. 5, when the pair of side compression bands 800 form elasticity to be pulled away from the coupling member 300, the coupling member 300 may be elastically stretched. Even if both breasts of the patient 11 are spaced apart from each other, the pair of cups 100 and 200 stably cover both breasts, respectively, by the elasticity of the coupling member 300.

F1 illustrated in FIG. 7 represents the elasticity of the pair of side compression bands 800 for pulling the pair of cups 100 and 200 away from the coupling member 300, respectively, while covering the breasts. As illustrated in FIG. 7, by adjusting the positions on the pair of back bands 400 to which the other ends of the pair of side compression bands 800 are coupled, one breast of the patient may be spaced apart from the contra-lateral breast. That is, as the intensity of F1 is changed, the positions of the breasts may be changed.

As illustrated in FIG. 2, holes H may be formed in the pair of side bands 500 and the pair of side compression bands 800, so that a set-up line on the skin of the patient may be seen through the holes H.

As illustrated in FIGS. 2 and 3, the pair of shoulder bands 600 are also configured to compress the breasts of the patient 11 while being on the pair of cups 100 and 200.

One ends of the pair of shoulder bands 600 are coupled to the pair of cups 100 and 200, respectively, at the lower sides of the breasts. The one ends of the pair of shoulder bands 600 may be coupled to the edges of the pair of cups 100 and 200, respectively, through sewing, bonding, or heat fusion. Alternatively, the pair of cups 100 and 200 and the pair of shoulder bands 600 may be integrally manufactured. The pair of shoulder bands 600 may be made of the air equivalent material.

The pair of shoulder bands 600 may be made of the carbon fiber woven in the mesh shape. When made of the carbon fiber, since the pair of shoulder bands 600 exhibit the same ionization effect for radiation as air, the pair of shoulder bands 800 do not affect the radiation dose irradiated to the lesion sites of the breasts.

When the pair of shoulder bands 600 are woven in the mesh shape, deformation of the pair of shoulder bands 600 is facilitated by applying an external force to the pair of shoulder bands 600. As a result, it is possible to easily adjust the compression force of the pair of shoulder bands 600 by the external force.

As illustrated in FIG. 3, the other ends of the pair of shoulder bands 600 are detachably coupled to the pair of back bands 400, respectively. The pair of shoulder bands 600 and the pair of back bands 400 are detachably coupled to each other by the hook K or Velcro V. The middle portions of the pair of shoulder bands 600 are configured to be in close contact with both shoulders of the patient 11. As illustrated in FIG. 3, the positions on the pair of back bands 400 to which the pair of shoulder bands 600 are detachably coupled may be adjusted in various directions, such as the horizontal and vertical directions.

The pair of shoulder bands 600 are formed in a long strap shape as a whole. The pair of shoulder bands 600 are formed to have a wider width toward the coupling member 300. As a result, the pair of shoulder bands 600 are formed to cover the breasts while being on the pair of cups 100 and 200.

As illustrated in FIG. 6, when the other ends of the pair of shoulder bands 600 are coupled to the pair of back bands 400, respectively, the pair of shoulder bands 600 move the lower breast tissues in the direction of each of the nipples and reduce a transmission range of the radiation dose, by forming elasticity for pulling the lower sides of the pair of cups 100 and 200 upward while covering the breasts, thereby reducing transmission of the radiation dose to the lung and the heart positioned in the direction of the tumor.

The pair of shoulder bands 600 are configured to compress the breasts of the patient 11 while maintaining the tensile force applied thereto.

By adjusting the positions on the pair of back bands 400 to which the other ends of the pair of shoulder bands 600 are coupled, it is possible to adjust a force of the pair of shoulder bands 600 for compressing the breasts of the patient 11 while being on the pair of cups 100 and 200. As a result, it is possible to compress the breasts of the patient 11 enough to flatten the irregularities of breast skin tissue without excessively compressing a chest of the patient 11.

In addition, it is possible to stably support the breasts with an appropriate compression force despite a size change of the breasts and chest circumference or a size change of only one breast resulting from a weight change of the patient 11.

F2 illustrated in FIG. 8 represents the elasticity of the pair of shoulder bands 600 for pulling the pair of cups 100 and 200. As illustrated in FIG. 8, by adjusting the positions on the pair of back bands 400 to which the other ends of the pair of side compression bands 800 and the other ends of the pair of shoulder bands 600 are coupled, it is possible to move the breasts of the patient upward. That is, as F1 and F2 are changed, the positions of the breasts may be changed.

As illustrated in FIG. 6, one ends of the pair of shoulder bands 600 are coupled to the lower portions of the pair of cups 100 and 200, respectively. One ends of the pair of side bands 500 are also coupled to the lower portions of the pair of cups 100 and 200, respectively. One ends of the pair of shoulder bands 600 and one ends of the pair of side bands 500 are coupled to the same lower portions (or adjacent lower portions) of the pair of cups 100 and 200, respectively. As a result, it is possible to prevent the lower portions of the pair of cups 100 and 200 from being lifted due to the tensile force of the pair of shoulder bands 600.

The brassiere for radiation therapy 10 may be put on in the following order.

As illustrated in FIG. 4, the patient 11 covers the breasts with the first cup 100 and the second cup 200, respectively, and then couples the first band 410 and the second back band 420 to each other at his or her back. The state in which the first cup 100 and the second cup 200 cover the breasts of the patient 11 is maintained by the elasticity of the pair of cups 100 and 200, the coupling member 300, and the pair of side bands 500.

As illustrated in FIG. 5, when the other ends of the pair of side compression bands 800 are coupled to the pair of back bands 400, respectively, the pair of side compression bands 800 form elasticity for pulling the pair of cups 100 and 200 away from the coupling member 300 while covering the breasts. The pair of side compression bands 800 are configured to compress the breasts of the patient 11 while maintaining the tensile force applied thereto.

As illustrated in FIG. 6, when the other ends of the pair of shoulder bands 600 are coupled to the pair of back bands 400, respectively, the pair of shoulder bands 600 form elasticity for pulling the lower portions of the pair of cups 100 and 200 upward while covering the breasts. The pair of shoulder bands 600 are configured to compress the breasts of the patient 11 while maintaining the tensile force applied thereto.

Referring to FIG. 6, the breasts are fixed by the force of the pair of side compression bands 800 for pulling the pair of cups 100 and 200 in a 90° direction and the force of the pair of shoulder bands 600 for pulling the pair of cups 100 and 200 in a 135° direction. By adjusting the positions on the pair of back bands 400 to which the other ends of the pair of side compression bands 800 and the other ends of the pair of shoulder bands 600 are coupled, it is possible to variously adjust the force of the pair of side compression bands 800 and the pair of shoulder bands 600 for compressing the breasts of the patient 11 while being on the pair of cups 100 and 200.

As a result, it is possible to compress the breasts of the patient 11 enough to flatten irregularities of the breast skin tissue without excessively compressing the chest of the patient 11. In addition, it is possible to stably support both breasts with the appropriate compression force despite a size change of the breasts and chest circumference or a size change of only one breast resulting from the weight change of the patient 11.

In addition, as illustrated in FIGS. 7 and 8, by adjusting the intensity and direction of the force of the pair of side compression bands 800 and the pair of shoulder bands 600 for pulling the pair of cups 100 and 200 through adjusting the positions on the pair of back bands 400 to which the other ends of the pair of side compression bands 800 and the other ends of the pair of shoulder bands 600 are coupled, it is possible to move the breasts of the patient in various directions, such as horizontal and vertical directions. That is, as F1 and F2 are changed, the positions of the breasts may be changed.

Second Embodiment

As illustrated in FIG. 1, when performing radiation therapy on the totally mastectomized part of the patient (not shown), the patient lies on the couch 2, and the radiation generated by the device for radiation therapy 3 is irradiated to the lesion site of the totally mastectomized part.

Figure 9:
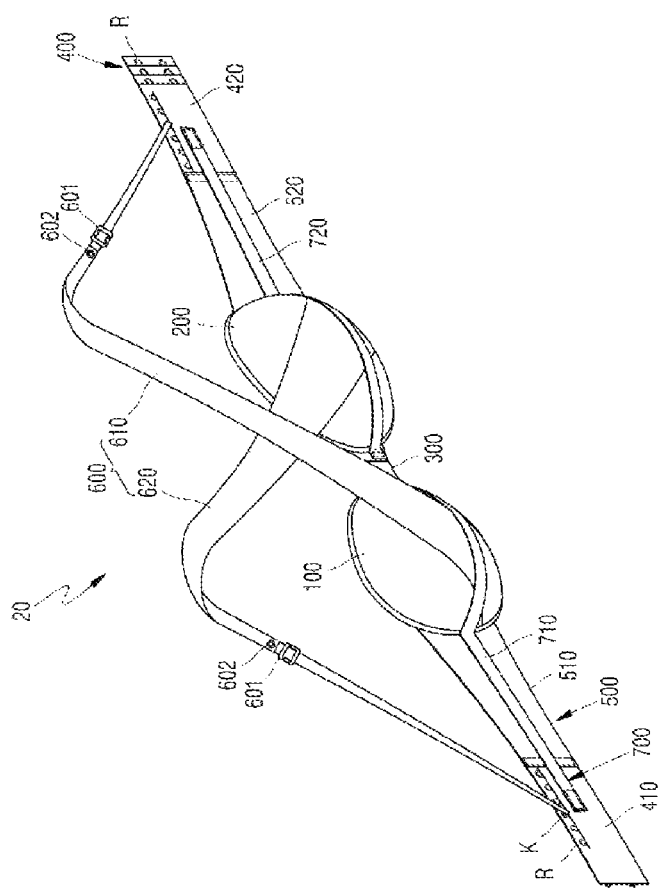
FIG. 9 is a front perspective view of a brassiere for radiation therapy according to a second embodiment of the present disclosure.
Figure 10:
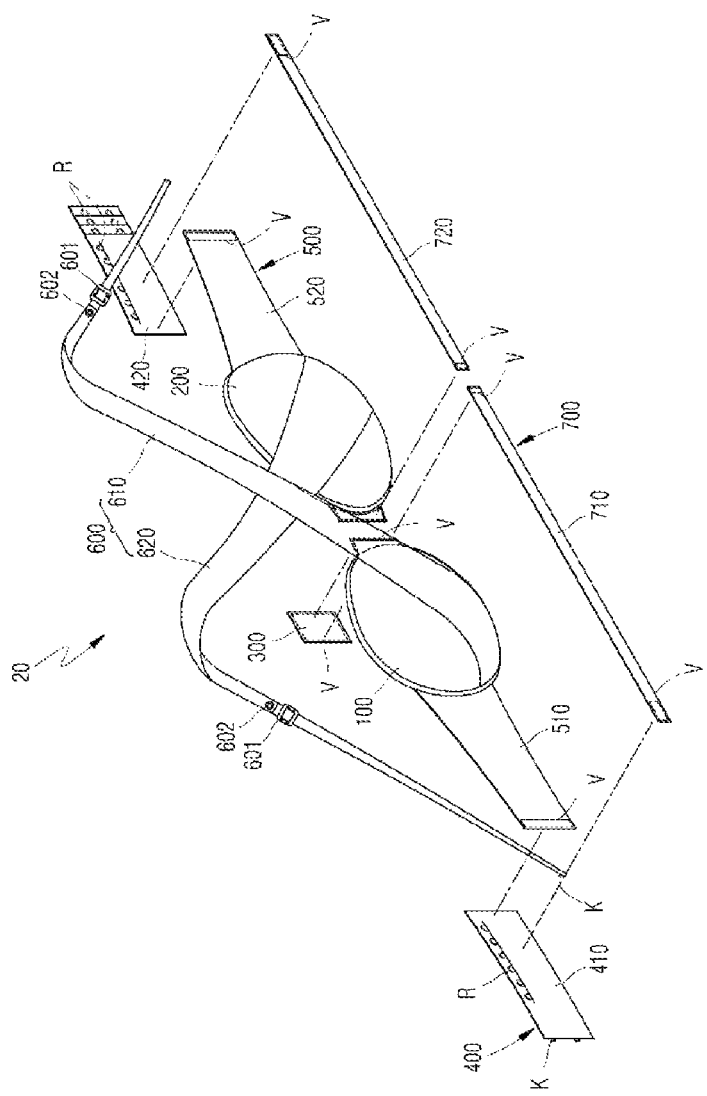
FIG. 10 is an exploded perspective view of the brassiere for radiation therapy of FIG. 9.
Figure 11:
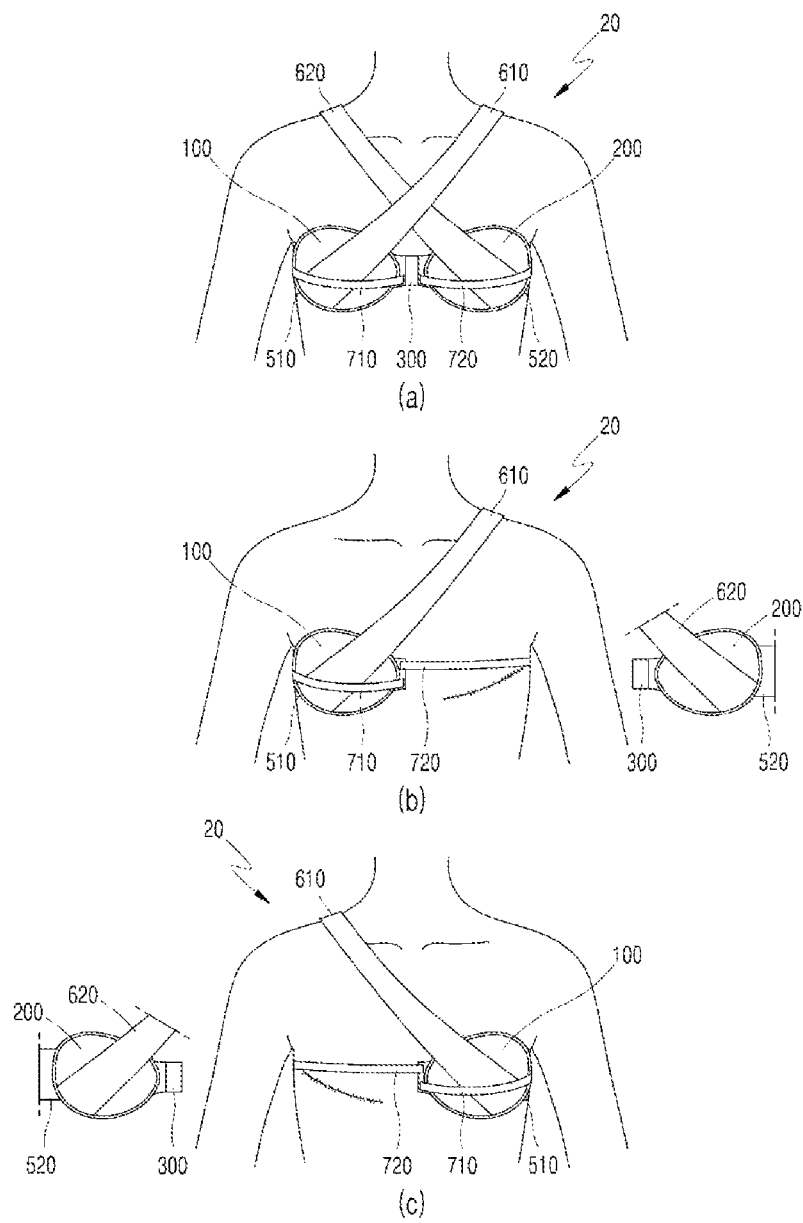
FIG. 11 is a view illustrating a state in which the brassiere for radiation therapy of FIG. 9 is worn.

FIG. 9 is a front perspective view of a brassiere for radiation therapy 20 according to the second embodiment of the present disclosure. FIG. 10 is an exploded perspective view of the brassiere for radiation therapy 20 of FIG. 9. FIG. 11 is a view illustrating a state in which the brassiere for radiation therapy 20 of FIG. 9 is worn.

The brassiere for radiation therapy 20 according to the second embodiment of the present disclosure is configured to prevent an intact breast from being visually exposed during radiation therapy for one breast.

As illustrated in FIGS. 9 to 11, the brassiere for radiation therapy 20 according to the second embodiment of the present disclosure includes the first cup 100, the second cup 200, the coupling member 300, the pair of back bands 400, a first side band 510, a second side band 520, a first shoulder band 610, a second shoulder band 620, and a pair of coupling bands 700.

As illustrated in FIG. 11(a), the first cup 100 is configured to cover one breast (the intact breast) of the patient. In addition, the second cup 200 is configured to cover a mastectomized breast of the patient in normal situations. The first cup 100 and the second cup 200 may form a symmetrical shape with respect to the coupling member 300. In normal situations, a pad (not shown) for replacing the mastectomized breast of the patient may be inserted into the second cup 200.

When a left breast of the patient has been mastectomized, the first cup 100 may refer to a cup for covering a right breast of the patient, and the second cup 200 may refer to a cup for covering the mastectomized breast of the patient. As illustrated in FIG. 11(b), when performing radiation therapy on the mastectomized breast, the second cup 200 is separated from the brassiere for radiation therapy 20. Therefore, medical staff may perform radiation therapy while visually observing the mastectomized breast.

When the right breast of the patient has been mastectomized, the first cup 100 may refer to a cup for covering the left breast of the patient, and the second cup 200 may refer to a cup for covering the mastectomized breast of the patient. As illustrated in FIG. 11(c), when performing radiation therapy on the mastectomized breast, the second cup 200 is separated from the brassiere for radiation therapy 20. Therefore, medical staff may perform radiation therapy while visually observing the mastectomized breast.

As illustrated in FIGS. 9 and 10, the first cup 100 and the second cup 200 are coupled to each other by the coupling member 300. The coupling member 300 is positioned between the first cup 100 and the second cup 200, and is configured to couple the first cup 100 and the second cup 200 to each other. Hereinafter, it should be understood that "cup" refers to the first cup 100 or the second cup 200.

Both ends of the coupling member 300 may be coupled to the first cup 100 and the second cup 200, respectively. The coupling member 300 and the pair of cups may be detachably coupled to each other by a hook or Velcro V. Alternatively, the coupling member 300 and the second cup 200 may be detachably coupled to each other by the hook or Velcro V, and the coupling member 300 and the first cup 100 may be maintained in a coupled state through sewing, bonding, or heat fusion.

The pair of cups and the coupling member 300 may be made of an air equivalent material. The air equivalent material refers to a material that has the same effective atomic number as air and exhibits the same ionization effect for radiation as air. Examples of air equivalent materials include graphite, paper, and certain plastics.

The pair of cups may be made of woven carbon fiber. When made of the carbon fiber, since the pair of cups exhibit the same ionization effect for radiation as air, the pair of cups does not affect the radiation dose irradiated to the lesion sites of the breasts.

As illustrated in FIGS. 9 and 10, the pair of back bands 400 are configured to be in close contact with the back of the patient, and include a first back band 410 and a second back band 420.

The first back band 410 and the second back band 420 are detachably coupled to each other by the hook K or Velcro V. The first back band 410 and the second back band 420 are formed in a strap shape, respectively. The first back band 410 and the second back band 420 are made of a fibrous material having elasticity. The pair of back bands 400 may also be made of the carbon fiber.

As illustrated in FIGS. 9 to 11, the pair of side bands 500 are provided on both flanks of the patient 11, respectively, and couple the pair of cups and the pair of back bands 400 to each other. The pair of side bands 500 include the first side band 510 and the second side band 520.

The first side band 510 extends from the first cup 100, and is detachably coupled to the first back band 410. The first side band 510 is provided at one flank of the patient, and couples the first cup 100 and the first back band 410 to each other.

The second side band 520 extends from the second cup 200, and is detachably coupled to the second back band 420. The second side band 520 is provided at the other flank of the patient, and couples the second cup 200 and the second back band 420 to each other. The pair of side bands 500 are configured to be in close contact with both flanks of the patient, respectively.

One end of the first side band 510 may be coupled to the first cup 100 at the opposite side thereof to the coupling member 300. One end of the second side band 520 may be coupled to the second cup 200 at the opposite side thereof to the coupling member 300. The one ends of the pair of side bands 500 may be coupled to the edges of the pair of cups, respectively, through sewing, bonding, or heat fusion.

Alternatively, the first cup 100 and the second cup 200 may be integrally manufactured with the pair of side bands 500. The pair of side bands 500 may be made of the air equivalent material.

By covering the breasts of the patient with the first cup 100 and the second cup 200 and coupling the first back band 410 and the second back band 420 to each other at the back of the patient, a state in which the breasts of the patient are covered with the first cup 100 and the second cup 200 can be maintained through the elasticity of the pair of cups, the coupling member 300, and the pair of side bands 500.

As illustrated in FIGS. 9 to 11, the pair of shoulder bands 600 are worn over both shoulders of the patient, and couple the pair of cups to the pair of back bands 400, respectively. The pair of shoulder bands 600 include the first shoulder band 610 and the second shoulder band 620.

One end of the first shoulder band 610 may be coupled to the first cup 100, and the other end of the first shoulder band 610 may be detachably coupled to the second back band 420. One end of the second shoulder band 620 may be coupled to the second cup 200, and the other end of the second shoulder band 620 may be detachably coupled to the first back band 410.

Figure 12:
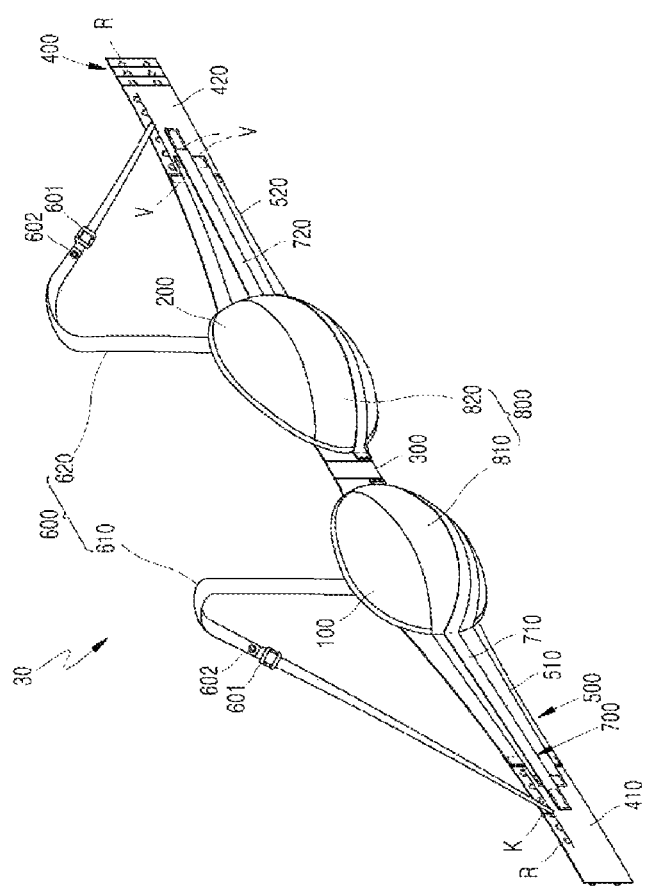
FIG. 12 is a front perspective view of a brassiere for radiation therapy according to a third embodiment of the present disclosure.
Figure 13:
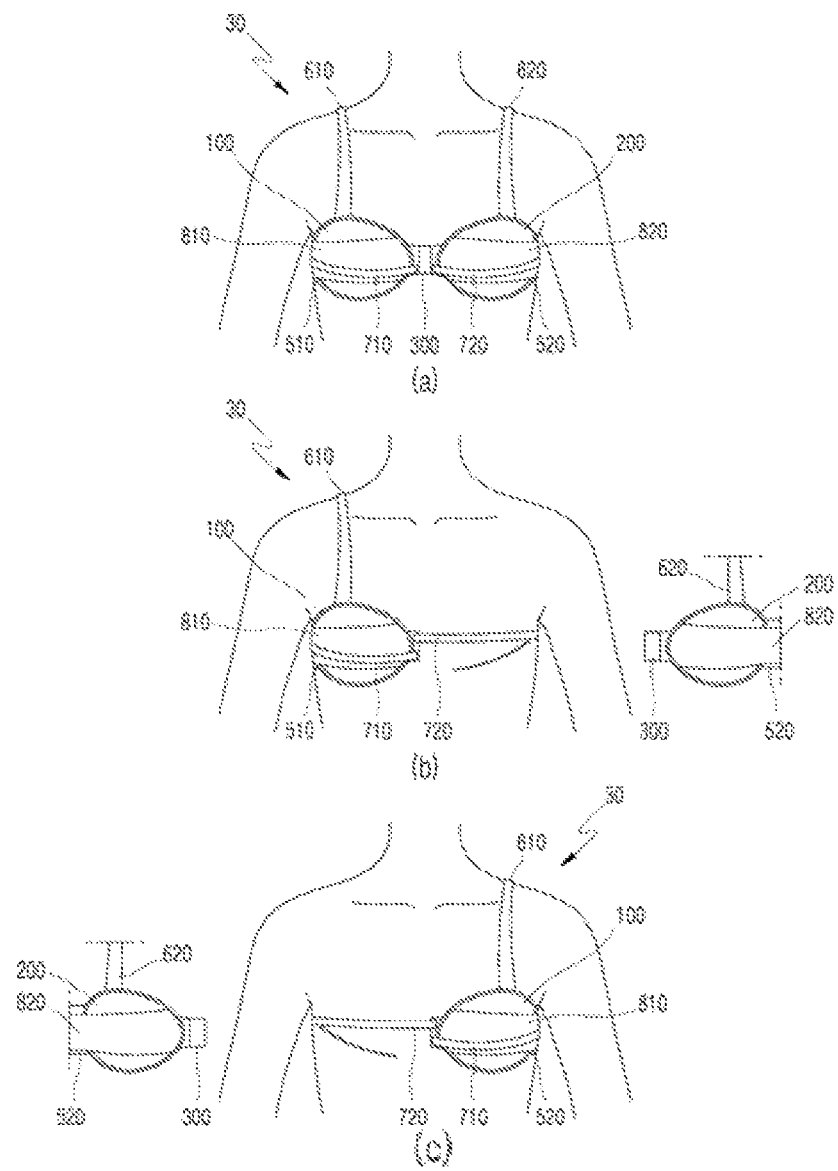
FIG. 13 is a view illustrating a state in which the brassiere for radiation therapy of FIG. 12 is worn.

Alternatively, as illustrated in FIGS. 12 and 13, one end of the first shoulder band 610 may be coupled to the first cup 100, and the other end of the first shoulder band 610 may be detachably coupled to the first back band 410. In addition, one end of the second shoulder band 620 may be coupled to the second cup 200, and the other end of the second shoulder band 620 may be detachably coupled to the second back band 420.

FIGS. 9 to 11 illustrate that the other end of the first shoulder band 610 is detachably coupled to the second back band 420, and the other end of the second shoulder band 620 is detachably coupled to the first back band 410.

One ends of the pair of shoulder bands 600 may be coupled to the pair of cups at the lower sides of the breasts, respectively. The one ends of the pair of shoulder bands 600 may be coupled to the edges of the pair of cups, respectively, through sewing, bonding, or heat fusion. Alternatively, the pair of cups and the pair of shoulder bands 600 may be integrally manufactured. The pair of shoulder bands 600 may be made of the air equivalent material.

The pair of shoulder bands 600 may be made of woven carbon fiber. When made of the carbon fiber, since the pair of shoulder bands 600 exhibit the same ionization effect for radiation as air, the pair of shoulder bands 600 do not affect the radiation dose irradiated to the lesion sites of the breasts.

As illustrated in FIG. 9, the other ends of the pair of shoulder bands 600 are detachably coupled to the pair of back bands 400, respectively. The pair of shoulder bands 600 and the pair of back bands 400 are detachably coupled to each other by the hook K or Velcro V. The middle portions of the pair of shoulder bands 600 are configured to be in close contact with both shoulders of the patient.

A plurality of rings R for detachably coupling the hook K to the pair of back bands 400 may be provided on the pair of back bands 400. As a result, the positions on the pair of back bands 400 to which the pair of shoulder bands 600 are detachably coupled may be adjusted in various directions, such as the horizontal and vertical directions. The pair of shoulder bands 600 are formed in a long strap shape as a whole.

Each the pair of shoulder bands 600 may be provided with an adjusting member 601. Medical staff may adjust the length of the first shoulder band 610 and the length of the second shoulder band 620 according to the body shape and height of the patient. As disclosed in Korean Patent Publication No. 2017-0083986, a device for adjusting the length of the shoulder strap of the brassiere is known, and thus a detailed description thereof will be omitted.

Each of the first shoulder band 610 and the second shoulder band 620 may be provided with a snap button 602. Each of the first shoulder band 610 and the second shoulder band 620 may be separated into two parts through the snap button 602, or the separated two parts thereof may be recombined through the snap button 602. The patient may separate each of the pair of shoulder bands 600 into two parts or recombine the separated two parts, through the snap button 602.

The pair of shoulder bands 600 are formed to have a wider width toward the coupling member 300. As a result, the pair of shoulder bands 600 are formed to cover the breasts while being on the pair of cups.

When the other ends of the pair of shoulder bands 600 are coupled to the pair of back bands 400, respectively, the pair of shoulder bands 600 may form elasticity for pulling the lower portions of the pair of cups upward while covering the breasts of the patient, and may stably support the breasts.

By adjusting the positions on the pair of back bands 400 to which the other ends of the pair of shoulder bands 600 are coupled, it is possible to adjust the direction and force of the pair of shoulder bands 600 for compressing the breasts of the patient while being on the pair of cups.

As a result, it is possible to stably support the intact breast and mastectomized breast with an appropriate compression force despite a size change of the intact breast or chest circumference resulting from the weight change of the patient. In addition, it is possible to isolate the intact breast of the patient from the radiation therapy site of the mastectomized breast.

As illustrated in FIGS. 9 to 11, the pair of coupling bands 700 couple the pair of cups and the pair of back bands 400 to each other. The pair of coupling bands 700 include a first coupling band 710 and a second coupling band 720.

The first coupling band 710 extends from the first cup 100, and is detachably coupled to the first back band 410. One end of the first coupling band 710 extending from the first cup 100 may be detachably coupled to the first cup 100 by the hook or Velcro V. The other end of the first coupling band 710 may be detachably coupled to the first back band 410 by the hook or Velcro V.

The second coupling band 720 extends from the second cup 200, and is detachably coupled to the second back band 420. One end of the second coupling band 720 extending from the second cup 200 may be detachably coupled to the second cup 200 by the hook or Velcro V. The other end of the second coupling band 720 may be detachably coupled to the second back band 420 by the hook or Velcro V.

The pair of coupling bands 700 may be made of the air equivalent material. The pair of coupling bands 700 may be made of woven carbon fiber. When made of the carbon fiber, since the pair of coupling bands 700 exhibit the same ionization effect for radiation as air, the pair of coupling bands 700 do not affect the radiation dose irradiated to the lesion sites of the breasts.

As illustrated in FIG. 11(*a*), the first coupling band 710 is formed to cover the breast while being on the first cup 100. The second coupling band 720 is formed to cover the breast while being on the second cup 200 in normal situations.

As described above, when performing radiation therapy on the mastectomized breast, the second cup 200, the second side band 520, and the second shoulder band 620 are separated from the brassiere for radiation therapy 20. At this time, one end of the second coupling band 720 is separated from the second cup 200, and is then attached to the first cup 100 by the hook or Velcro V.

Therefore, as illustrated in FIGS. 11(*b*) and 11(*c*), when performing radiation therapy on the mastectomized breast, the second coupling band 720 couples the first cup 100 and the second back band 420 to each other at the opposite side of the first side band 510. The pair of coupling bands 700 are formed in a thin strap shape. Therefore, medical staff may perform radiation therapy while visually observing the mastectomized breast.

When performing radiation therapy on the mastectomized breast, if the first cup 100 is coupled to one of the pair of back bands 400 only by the first side band 510 and the first shoulder band 610, the first cup 100 may be easily moved by an external force applied to the first cup 100, thus exposing the intact breast.

As illustrated in FIGS. 11(*b*) and 11(*c*), when performing radiation therapy on the mastectomized breast, if the second coupling band 720 couples the first cup 100 and the second back band 420 to each other at the opposite side of the first side band 510, it is possible to prevent the intact breast from being exposed even when an external force is applied to the first cup 10.

Third Embodiment

FIG. 12 is a front perspective view of a brassiere for radiation therapy according to a third embodiment of the present disclosure. FIG. 13 is a view illustrating a state in which the brassiere for radiation therapy of FIG. 12 is worn.

As illustrated in FIGS. 12 and 13, a brassiere for radiation therapy 30 according to the third embodiment of the present disclosure includes the first cup 100, the second cup 200, the coupling member 300, the pair of back bands 400, the first side band 510, the second side band 520, the first shoulder band 610, the second shoulder band 620, the pair of coupling bands 700, and the pair of side compression bands 800.

The brassiere for radiation therapy 30 according to the third embodiment of the present disclosure is substantially the same as the second embodiment except for the pair of shoulder bands 600 and the pair of side compression bands 800. Therefore, in order to facilitate understanding of the present disclosure, description of the same configurations as those of the second embodiment will be omitted below.

As illustrated in FIGS. 12 and 13, the pair of shoulder bands 600 are worn over both shoulders of the patient, and couple the pair of cups to the pair of back bands 400. The pair of shoulder bands 600 include the first shoulder band 610 and the second shoulder band 620.

As illustrated in FIGS. 12 and 13, one end of the first shoulder band 610 may be coupled to the first cup 100, and the other end of the first shoulder band 610 may be detachably coupled to the first back band 410. In addition, one end of the second shoulder band 620 may be coupled to the second cup 200, and the other end of the second shoulder band 620 may be detachably coupled to the second back band 420.

One ends of the pair of shoulder bands 600 may be coupled to the upper portions of the pair of cups, respectively. The pair of shoulder bands 600 and the pair of cups may be coupled to each other through sewing, bonding, or heat fusion. Alternatively, the pair of cups and the pair of shoulder bands 600 may be integrally manufactured. The pair of shoulder bands 600 may be made of the air equivalent material.

The pair of shoulder bands 600 may be made of woven carbon fiber. When made of the carbon fiber, since the pair of shoulder bands 600 exhibit the same ionization effect for radiation as air, the pair of shoulder bands 600 do not affect the radiation dose irradiated to the lesion sites of the breasts.

As illustrated in FIG. 12, the other ends of the pair of shoulder bands 600 are detachably coupled to the pair of back bands 400, respectively. The pair of shoulder bands 600 and the pair of back bands 400 are detachably coupled to each other by the hook K or Velcro V. The middle portions of the pair of shoulder bands 600 are configured to be in close contact with both shoulders of the patient.

A plurality of rings R for detachably coupling the hook K to the pair of back bands 400 may be provided on the pair of back bands 400. As a result, the positions on the pair of back bands 400 to which the pair of shoulder bands 600 are detachably coupled may be adjusted in various directions, such as the horizontal and vertical directions. The pair of shoulder bands 600 are formed in a long strip shape as a whole.

Each of the pair of shoulder bands 600 may be provided with the adjusting member 601. Medical staff may adjust the length of the first shoulder band 610 and the length of the second shoulder band 620 according to the body shape and a height of the patient. As disclosed in Korean Patent Publication No. 2017-0083986, the device for adjusting the length of the shoulder strap of the brassiere is known, and thus a detailed description thereof will be omitted.

Each of the first shoulder band 610 and the second shoulder band 620 may be provided with a snap button 602. Each of the first shoulder band 610 and the second shoulder band 620 may be separated into two parts through the snap button 602, or the separated two parts thereof may be recombined through the snap button 602. The patient may separate each of the pair of shoulder bands 600 into two parts or recombine the separated two parts, through the snap button 602.

As illustrated in FIGS. 12 and 13, the pair of side compression bands 800 are configured to compress the breasts of the patient while being on the pair of cups. The pair of side compression bands 800 include the first side compression band 810 and the second side compression band 820.

The first side compression band 810 is configured to compress the intact breast of the patient while being on the first cup 100.

One end of the first side compression band 810 is coupled to the first cup 100 at the coupling member 300. The one end of the first side compression band 810 may be coupled to an edge of the first cup 100 through sewing, bonding, or heat fusion. Alternatively, the first cup 100 and the first side compression band 810 may be integrally manufactured. The first side compression band 810 may be made of the air equivalent material.

The first side compression band 810 may be made of woven carbon fiber. When made of the carbon fiber, since the first side compression band 810 exhibits the same ionization effect for radiation as air, the first side compression band 810 does not affect the radiation dose irradiated to the lesion site of the mastectomized breast.

As illustrated in FIG. 12, the other end of the first side compression band 810 is detachably coupled to one of the pair of back bands 400. The first side compression bands 810 and one of the pair of back bands 400 are detachably coupled to each other by the hook K or Velcro V. A middle portion of the first side compression band 810 is configured to be in close contact with one flank of the patient.

The first side compression band 810 is formed in a long strap shape as a whole. The first side compression band 810 is formed to have a wider width toward the coupling member 300. Therefore, the first side compression band 810 is formed to cover the breast while being on the first cup 100.

When the other end of the first side compression band 810 is coupled to one of the pair of back bands 400, the first side compression band 810 forms elasticity for pulling the first cup 100 away from the coupling member 300 while covering the breast. The first side compression band 810 compresses the intact breast of the patient by maintaining the tensile force applied thereto, and thus isolates the intact breast of the patient from the lesion site of the contra-lateral mastectomized breast during radiation therapy.

By adjusting the position on one of the pair of back bands 400 to which the other end of the first side compression band 810 is coupled, it is possible to adjust a force of the first side compression band 810 for compressing the breast of the patient while being on the first cup 100. As a result, the first side compression band 810 may not excessively compress the chest of the patient. In addition, it is possible to stably support the intact breast with an appropriate compression force despite a size change of the breasts and chest circumference or a size change of only one breast resulting from the weight change of the patient.

When the first side compression band 810 forms elasticity to be pulled away from the coupling member 300, the coupling member 300 may be elastically stretched. By adjusting the position on one of the pair of back bands 400 to which the other end of the first side compression band 810 is coupled, it is possible to adjust a position of the intact breast of the patient during radiation therapy.

The second side compression band 820 is configured to compress the mastectomized breast of the patient while being on the second cup 200.

One end of the second side compression band 820 is coupled to the second cup 200 at the coupling member 300. The one end of the second side compression band 820 may be coupled to an edge of the second cup 200 through sewing, bonding, or heat fusion. Alternatively, the second cup 200 and the second side compression band 820 may be integrally manufactured. The second side compression band 820 may be made of the air equivalent material.

As illustrated in FIG. 12, the other end of the second side compression band 820 is detachably coupled to one of the pair of back bands 400. The second side compression band 820 and one of the pair of back bands 400 are detachably coupled to each other by the hook K or Velcro V. The middle portion of the second side compression band 820 is configured to be in close contact with the other flank of the patient.

The second side compression band 820 is formed in a long strap shape as a whole. The second side compression band 820 is formed to have a wider width toward the coupling member 300. Therefore, the second side compression band 820 is formed to cover the second cup 200.

When the other end of the second side compression band 820 is coupled to one of the pair of back bands 400, the second side compression band 820 forms elasticity for pulling the second cup 200 away from the coupling member 300 while covering the mastectomized breast of the patient. The second side compression band 820 compresses the mastectomized breast of the patient by maintaining the tensile force applied thereto in normal situations.

By adjusting the position on one of the pair of back bands 400 to which the other end of the second side compression band 820 is coupled, it is possible to adjust a force of the second side compression band 820 for compressing the mastectomized breast of the patient while being on the second cup 200. As a result, the second side compression band 820 may not excessively compress the chest of the patient. In addition, it is possible to stably support the mastectomized breast of the patient with an appropriate compression force despite a size change of the chest circumference resulting from the weight change of the patient.

Fourth Embodiment

Figure 14:
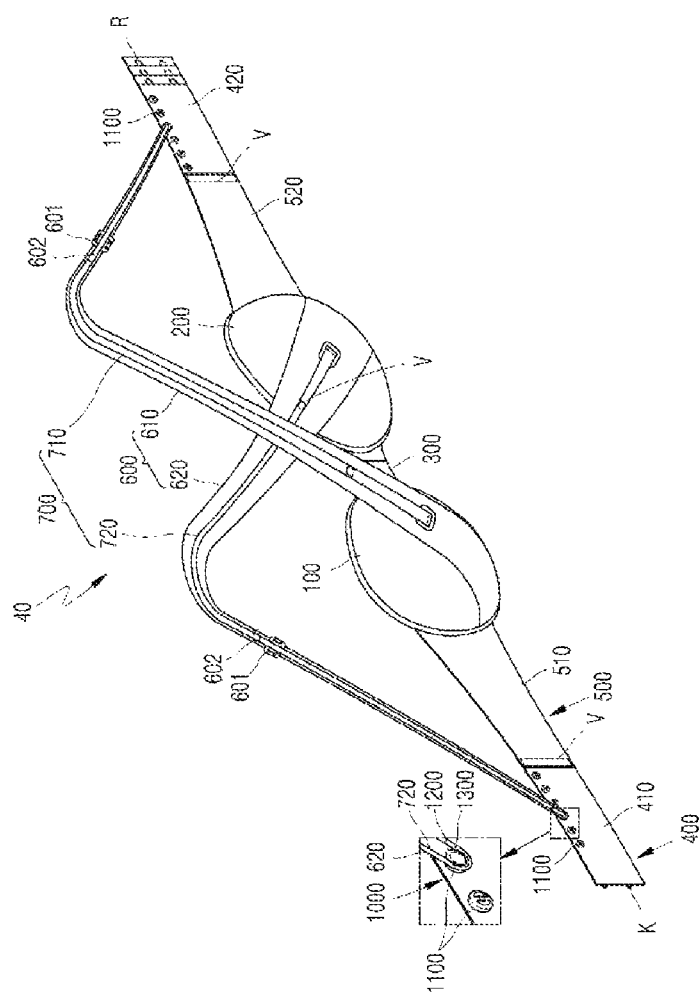
FIG. 14 is a front perspective view of a brassiere for radiation therapy according to a fourth embodiment of the present disclosure.
Figure 15:
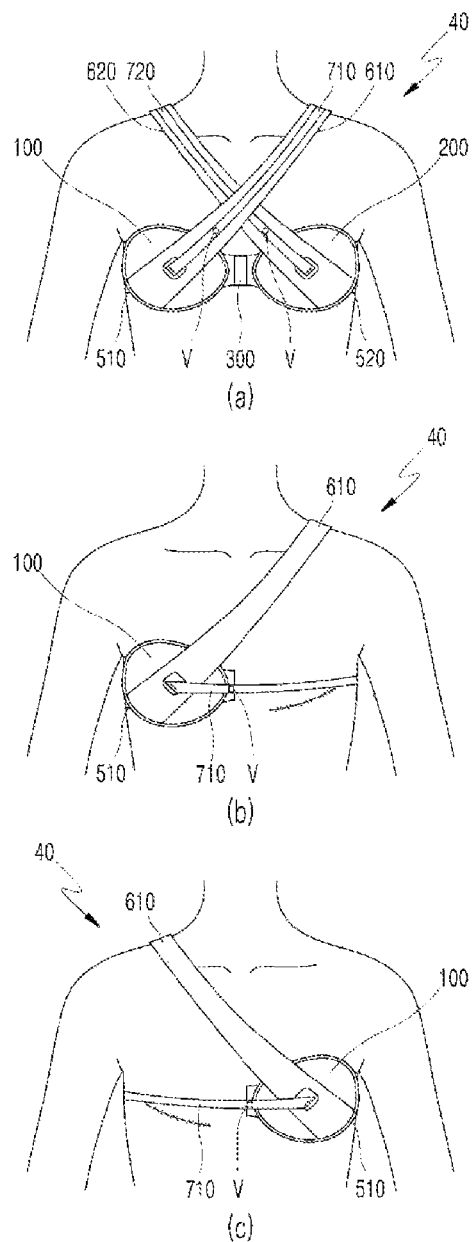
FIG. 15 is a view illustrating a state in which the brassiere for radiation therapy of FIG. 14 is worn.

FIG. 14 is a front perspective view of a brassiere for radiation therapy 40 according to the fourth embodiment of the present disclosure. FIG. 15 is a view illustrating a state in which the brassiere for radiation therapy 40 of FIG. 14 is worn.

As illustrated in FIGS. 14 and 15, the brassiere for radiation therapy 40 according to the fourth embodiment of the present disclosure includes the first cup 100, the second cup 200, the coupling member 300, the pair of back bands 400, the first side band 510, the second side band 520, the first shoulder band 610, the second shoulder band 620, and the pair of coupling bands 700.

As illustrated in FIG. 15(a), the first cup 100 is configured to cover one breast (the intact breast) of the patient. In addition, the second cup 200 is configured to cover the mastectomized breast of the patient in normal situations. The first cup 100 and the second cup 200 may form a symmetrical shape with respect to the coupling member 300. in normal situations, a pad (not shown) for replacing the mastectomized breast of the patient may be inserted into the second cup 200.

When the left breast of the patient has been mastectomized, the first cup 100 may refer to a cup for covering the right breast of the patient, and the second cup 200 may refer to a cup for covering the mastectomized breast of the patient.

As illustrated in FIG. 15(b), when performing radiation therapy on the mastectomized breast, the second cup 200 is separated from the brassiere for radiation therapy 40. Therefore, medical staff may perform radiation therapy while visually observing the mastectomized breast.

When the right breast of the patient has been mastectomized, the first cup 100 may refer to a cup for covering the left breast of the patient, and the second cup 200 may refer to a cup for covering the mastectomized breast of the patient.

As illustrated in FIG. 15(c), when performing radiation therapy on the mastectomized breast, the second cup 200 is separated from the brassiere for radiation therapy 40. Therefore, medical staff may perform radiation therapy while visually observing the mastectomized breast.

As illustrated in FIG. 14, the first cup 100 and the second cup 200 are coupled to each other by the coupling member 300. The coupling member 300 is positioned between the first cup 100 and the second cup 200, and is configured to couple the first cup 100 and the second cup 200 to each other.

Both ends of the coupling member 300 may be coupled to the first cup 100 and the second cup 200, respectively. The coupling member 300 and the pair of cups may be detachably coupled to each other by the hook or Velcro V. Alternatively, the coupling member 300 and the second cup 200 may be detachably coupled to each other by the hook or Velcro V, and the coupling member 300 and the first cup 100 may be maintained in a coupled state through sewing, bonding, or heat fusion.

The pair of cups and the coupling member 300 may be made of the air equivalent material. The air equivalent material refers to a material that has the same effective atomic number as air and exhibits the same ionization effect for radiation as air. Examples of air equivalent materials include graphite, paper, and certain plastics.

The pair of cups may be made of woven carbon fiber. When made of the carbon fiber, since the pair of cups exhibit the same ionization effect for radiation as air, the pair of cups do not affect the radiation dose irradiated to the lesion sites of the breasts.

As illustrated in FIG. 14, the pair of back bands 400 are configured to be in close contact with the back of the patient, and include the first back band 410 and the second back band 420.

The first back band 410 and the second back band 420 are detachably coupled to each other by the hook K or Velcro V. The first back band 410 and the second back band 420 are formed in a strap shape, respectively. The first back band 410 and the second back band 420 are made of a fibrous material having elasticity. The pair of back bands 400 may also be made of the carbon fiber.

As illustrated in FIGS. 14 and 15, the pair of side bands 500 are provided on both flanks of the patient 11, respectively, and couple the pair of cups and the pair of back bands 400 to each other. The pair of side bands 500 include the first side band 510 and the second side band 520.

The first side band 510 extends from the first cup 100, and is detachably coupled to the first back band 410. The first side band 510 is provided on one flank of the patient, and couples the first cup 100 and the first back band 410 to each other.

The second side band 520 extends from the second cup 200, and is detachably coupled to the second back band 420. The second side band 520 is provided on the other flank of the patient, and couples the second cup 200 and the second back band 420 to each other. The pair of side bands 500 are configured to be in close contact with both flanks of the patient, respectively.

One end of the first side band 510 may be coupled to the first cup 100 at the opposite side thereof to the coupling member 300. One end of the second side band 520 may be coupled to the second cup 200 at the opposite side thereof to the coupling member 300. The one ends of the pair of side bands 500 may be coupled to the edges of the pair of cups, respectively, through sewing, bonding, or heat fusion.

Alternatively, the first cup 100 and the second cup 200 may be integrally manufactured with the pair of side bands 500. The pair of side bands 500 may be made of the air equivalent material.

By covering the breasts of the patient with the first cup 100 and the second cup 200 and coupling the first back band 410 and the second back band 420 to each other at the back of the patient, a state in which the breasts of the patient are covered with the first cup 100 and the second cup 200 can be maintained through the elasticity of the pair of cups, the coupling member 300, and the pair of side bands 500.

As illustrated in FIGS. 14 and 15, the pair of shoulder bands 600 are worn over both shoulders of the patient, and couple the pair of cups to the pair of back bands 400. The pair of shoulder bands 600 includes the first shoulder band 610 and the second shoulder band 620.

One end of the first shoulder band 610 may be coupled to the first cup 100, and the other end of the first shoulder band 610 may be detachably coupled to the second back band 420. One end of the second shoulder band 620 may be coupled to the second cup 200, and the other end of the second shoulder band 620 may be detachably coupled to the first back band 410.

Alternatively, as illustrated in FIGS. 12 and 13, one end of the first shoulder band 610 may be coupled to the first cup 100, and the other end of the first shoulder band 610 may be detachably coupled to the first back band 410. In addition, one end of the second shoulder band 620 may be coupled to the second cup 200, and the other end of the second shoulder band 620 may be detachably coupled to the second back band 420.

FIGS. 14 and 15 illustrate that the other end of the first shoulder band 610 is detachably coupled to the second back band 420, and the other end of the second shoulder band 620 is detachably coupled to the first back band 410.

One ends of the pair of shoulder bands 600 may be coupled to the pair of cups at the lower sides of the breasts, respectively. The one ends of the pair of shoulder bands 600 may be coupled to the edges of the pair of cups, respectively, through sewing, bonding, or heat fusion. Alternatively, the pair of cups and the pair of shoulder bands 600 may be integrally manufactured. The pair of shoulder bands 600 may be made of the air equivalent material.

The pair of shoulder bands 600 may be made of woven carbon fiber. When made of the carbon fiber, since the pair of shoulder bands 600 exhibit the same ionization effect for radiation as air, the pair of shoulder bands 600 do not affect the radiation dose irradiated to the lesion sites of the breasts.

As illustrated in FIG. 14, the other ends of the pair of shoulder bands 600 are detachably coupled to the pair of back bands 400, respectively. The pair of shoulder bands 600 and the pair of back bands 400 are detachably coupled to each other by a snap button 1000. The middle portions of the pair of shoulder bands 600 are configured to be in close contact with both shoulders of the patient.

The other ends of the pair of shoulder bands 600 may be provided with a first male snap 1200. The pair of back bends 400 may be provided with a plurality of female snaps 1100. The first male snap 1200 may be detachably coupled to one of the plurality of female snaps 1100. As a result, the positions on the pair of back bands 400 to which the pair of shoulder bands 600 are detachably coupled may be adjusted in various directions, such as the horizontal and vertical directions. The pair of shoulder bands 600 are formed in a long strip shape as a whole.

Each of the pair of shoulder bands 600 may be provided with the adjusting member 601. Medical staff may adjust the length of the first shoulder band 610 and the length of the second shoulder band 620 according to the body shape and height of the patient. As disclosed in Korean Patent Publication No. 2017-0083986, the device for adjusting the length of the shoulder strap of the brassiere is known, and thus a detailed description thereof will be omitted.

Each of the first shoulder band 610 and the second shoulder band 620 may be provided with the snap button 602. Each of the first shoulder band 610 and the second shoulder band 620 may be separated into two parts through the snap button 602, or the separated two parts thereof may be recombined through the snap button 602. The patient may separate each of the pair of shoulder bands 600 into two parts or recombine the separated two parts, through the snap button 602.

The pair of shoulder bands 600 are formed to have a wider width toward the coupling member 300. As a result, the pair of shoulder bands 600 are formed to cover the breasts while being on the pair of cups.

When the other ends of the pair of shoulder bands 600 are coupled to the pair of back bands 400, respectively, the pair of shoulder bands 600 may form elasticity for pulling the lower portions of the pair of cups upward while covering the breasts of the patient, and may stably support the breasts.

By adjusting the positions on the pair of back bands 400 to which the other ends of the pair of shoulder bands 600 are coupled, it is possible to adjust the direction and force of the pair of shoulder bands 600 for compressing the breasts of the patient while being on the pair of cups.

As a result, it is possible to stably support the intact breast and mastectomized breast with an appropriate compression force despite a size change of the intact breast or chest circumference resulting from the weight change of the patient. In addition, it is possible to isolate the intact breast of the patient from the radiation therapy site of the mastectomized breast.

As illustrated in FIGS. 14 and 15, the pair of coupling bands 700 couple the pair of cups and the pair of back bands 400 to each other. The pair of coupling bands 700 include a first coupling band 710 and a second coupling band 720.

The first coupling band 710 extends from the first cup 100, and is detachably coupled to the second back band 420. One end of the first coupling band 710 extending from the first cup 100 may be coupled to the first cup 100.

The second coupling band 720 extends from the second cup 200, and is detachably coupled to the first back band 410. One end of the second coupling band 720 extending from the second cup 200 may be coupled to the second cup 200.

The other ends of the pair of coupling bands 700 may be provided with a second male snap 1300. The second male snap 1300 may be detachably coupled to one of a plurality of female snaps 1100.

The pair of coupling bands 700 may be made of the air equivalent material. The pair of coupling bands 700 may be made of woven carbon fiber. When made of the carbon fiber, since the pair of coupling bands 700 exhibit the same ionization effect for radiation as air, the pair of coupling bands 700 do not affect the radiation dose irradiated to the lesion sites of the breasts.

As illustrated in FIG. 15(a), the middle portion of the first coupling band 710 may be configured to be in close contact with one shoulder of the patient in normal situations. The middle portion of the second coupling band 720 may be configured to be in close contact with the other shoulder of the patient in normal situations.

When performing radiation therapy on the mastectomized breast, the second cup 200, the second side band 520, the second shoulder band 620, and the second coupling band 720 are separated from the brassiere for radiation therapy 40.

At this time, the first coupling band 710 is passed to the flank of the patient where the second side band 520 was present. As a result, the first coupling band 710 is provided on the flank of the patient where the second side band 520 was present, and couples the first cup 100 and the first back band 410 to each other.

Therefore, as illustrated in FIGS. 15(b) and 15(c), when performing radiation therapy on the mastectomized breast, the first coupling band 710 couples the first cup 100 and the second back band 420 to each other at the opposite side of the first side band 510. The pair of coupling bands 700 are formed in a thin strap shape. Therefore, medical staff may perform radiation therapy while visually observing the mastectomized breast.

When performing radiation therapy on the mastectomized breast, if the first cup 100 is coupled to one of the pair of back bands 400 only by the first side band 510 and the first shoulder band 610, the first cup 100 may be easily moved by an external force applied to the first cup 100, thus exposing the intact breast.

As illustrated in FIGS. 15(b) and 15(c), when performing radiation therapy on the mastectomized breast, if the first coupling band 710 couples the first cup 100 and the second back band 420 to each other at the opposite side of the first side band 510, it is possible to prevent the intact breast from being exposed even when an external force is applied to the first cup 10.

Figure 16:
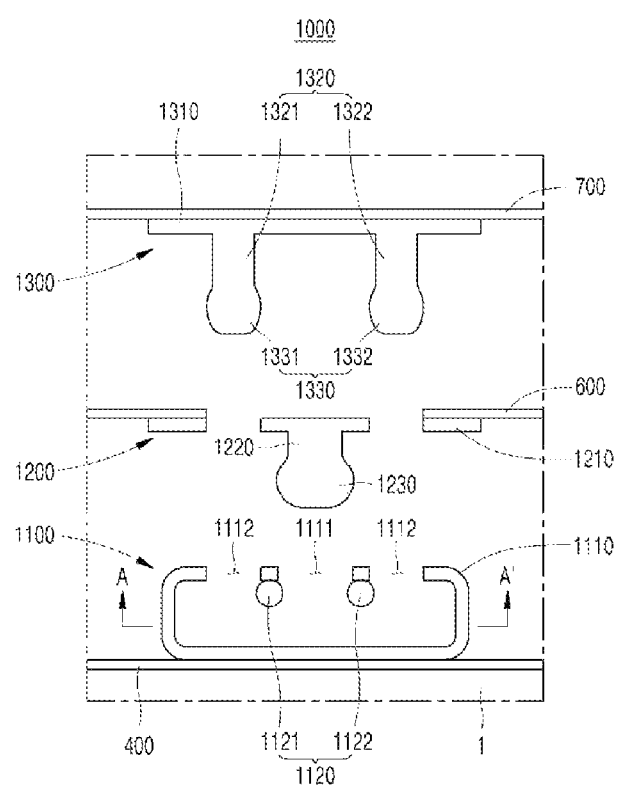
FIG. 16 is a cross-sectional view illustrating a separated state of a snap button of FIG. 14.
Figure 17:
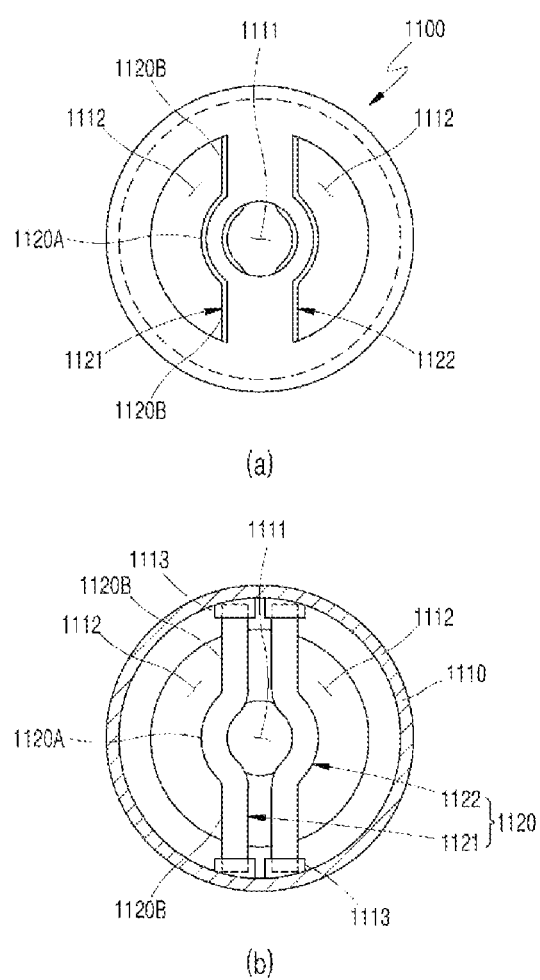
FIG. 17 is a view illustrating a female snap of FIG. 16.

FIG. 16 is a cross-sectional view illustrating a separated state of the snap button 1000 of FIG. 14. FIG. 17 is a view illustrating the female snap 1100 of FIG. 16. FIG. 17(a) is a plan view of the female snap 1100 of FIG. 16. FIG. 17(b) is a cross-sectional view taken along line A-A' of FIG. 16

Figure 18:
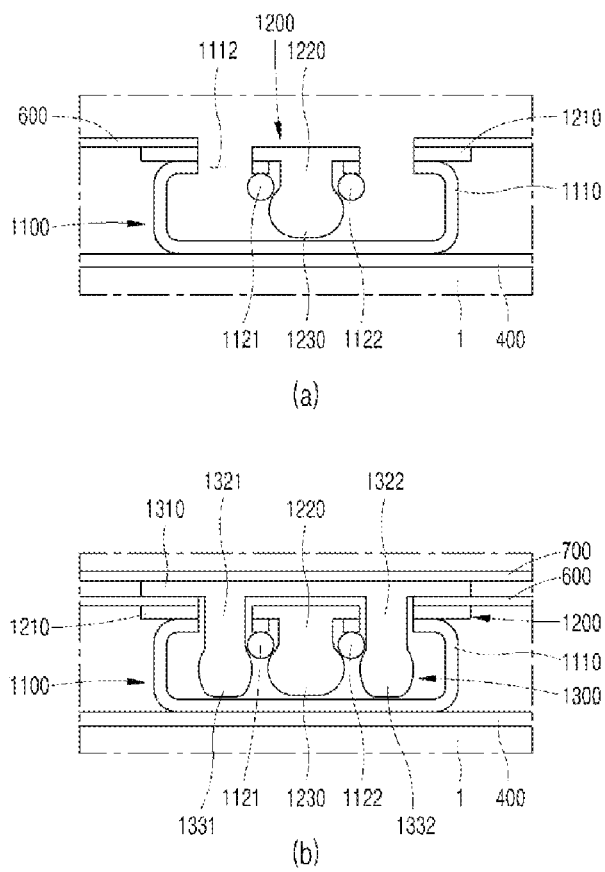
FIG. 18 is a cross-sectional view sequentially illustrating a process of coupling a snap button of FIG. 14.

FIG. 18 is a cross-sectional view sequentially illustrating a process of coupling the snap button 1000 of FIG. 14. Reference numeral "1" in FIGS. 16 and 18 designates the back (skin) of the patient.

Figure 19:
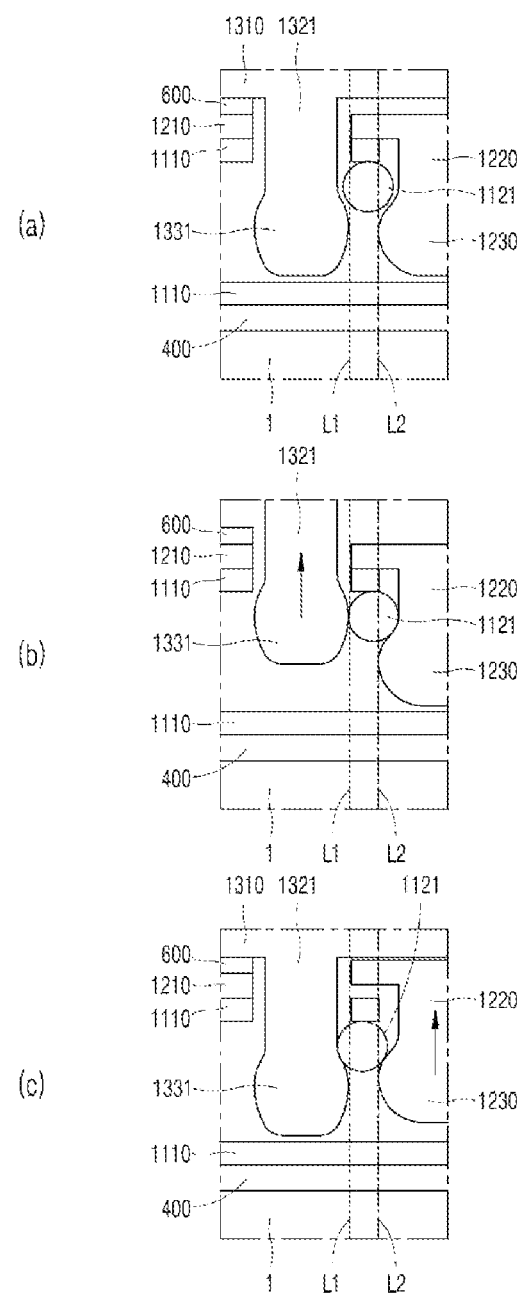
FIG. 19 is a partially enlarged view of FIG. 18(*b*).

FIG. 19 is a partially enlarged view of FIG. 18(b). FIG. 19(a) illustrates a state in which no external force is applied to the first male snap 1200 and the second male snap 1300.

FIG. 19(b) illustrates a state in which an external force that causes the second male snap 1300 to move away from one of the female snaps 1100 is applied to the second male snap 1300. FIG. 19(c) illustrates a state in which the external force that causes the first male snap 1200 to move away from one of the female snaps 1100 is applied to the first male snap 1200.

As illustrated in FIGS. 16 to 18, the first shoulder band 610 and the first coupling band 710 are detachably coupled to the second back band 420 by the snap button 1000.

The snap button 1000 includes female snaps 1100, a first male snap 1200, and a second male snap 1300. The female snaps 1100 are provided on the pair of back bands 400. The first male snap 1200 is provided on the first shoulder band 610. The second male snap 1300 is provided on the first coupling band 710.

As illustrated in FIGS. 16 to 18, each of the female snaps 1100 includes a housing 1110 and flexural deformable members 1120.

The housing 1110 is coupled to each of the pair of back bands 400. The housing 1110 has a space formed therein. The housing 1110 has a first through hole 1111 and a second through hole 1112. The first through hole 1111 may have a circular shape.

The second through hole 1112 is formed to surround the first through hole 1111. The second through hole 1112 may be formed along the circumferential direction of the first through hole 1111 around the first through hole 1111.

The flexural deformable members 1120 may be manufactured by bending a long elastic bar. The flexural deformable members 1120 include a first flexural deformable member 1121 and a second flexural deformable member 1122.

Each of the first flexural deformable member 1121 and the second flexural deformable member 1122 includes a contacting portion 1120A and a connecting portion 1120B.

The contacting portion 1120A refers to a portion by which a first expanding portion 1230 and second expanding portions 1330 are caught. The contacting portion 1120A of each of the first flexural deformable member 1121 and the second flexural deformable member 1122 may form a specific radius of curvature.

The connecting portion 1120B refers to a portion extending from both ends of the contacting portion 1120A. The connecting portion 1120B is fixed to the coupling portion 1113 of the housing 1110.

As illustrated in FIGS. 16 and 18, the first male snap 1200 includes a first body 1210, a first extending portion 1220, and a first expanding portion 1230.

The first body 1210 refers to a portion coupled to the first shoulder band 610. The first body 1210 may be formed in a disk shape. The first body 1210 may be coupled to the first shoulder band 610, for example, by an adhesive or by sewing.

The first extending portion 1220 couples the first body 1210 and the first expanding portion 1230 to each other. The first extending portion 1220 may be formed in a cylindrical shape. The first extending portion 1220 extends from the first body 1210. The first extending portion 1220 is not caught by the flexural deformable members 1120.

The first expanding portion 1230 is formed at an end of the first extending portion 1220. The first expanding portion 1230 refers to a portion that is caught by the flexural deformable members 1120. The first expanding portion 1230 may be formed in a ball shape. The first expanding portion 1230 has a larger radius than the first extending portion 1220 in the radial direction of the first extending portion 1220.

As illustrated in FIGS. 16 and 18, the second male snap 1300 includes a second body 1310, a second extending portion 1320, and the second expanding portions 1330.

The second body 1310 refers to a portion coupled to the first coupling band 710. The second body 1310 may be formed in a disk shape. The second body 1310 may be coupled to the second shoulder band 620, for example, by an adhesive or by sewing.

The second extending portions 1320 extend from the second body 1310. The second extending portions 1320 couple the second body 1310 and the second expanding portions 1330 to each other. The second extending portions 1320 may be formed in a cylindrical shape. The second extending portions 1320 are not caught by the flexural deformable members 1120.

The second extending portions 1320 include a second extending portion A 1321 and a second extending portion B 1322. The second extending portion A 1321 and the second extending portion B 1322 extend parallel to each other from the second body 1310.

The second expanding portions 1330 are formed at the ends of the second extending portions 1320. The second expanding portions 1330 refer to portions that are caught by the flexural deformable members 1120. The second expanding portions 1330 may be formed in a ball shape. The second expanding portions 1330 have a larger radius than the second extending portions 1320 in the radial direction of the second extending portions 1320.

The second expanding portions 1330 include a second expanding portion A 1331 formed in the second extending portion A 1321 and a second expanding portion B 1332 formed in the second extending portion B 1322. As illustrated in FIG. 18, the second expanding portion A 1331 is caught by the contacting portion 1120A of the first flexural deformable member 1121. The second expanding portion B 1332 is caught by the contacting portion 1120A of the second flexural deformable member 1122.

As illustrated in FIG. 18(a), when the brassiere for radiation therapy 40 is worn, the first male snap 1200 is coupled to one of the female snaps 1100, and then, as illustrated in FIG. 18(*b*), the second male snap 1300 is coupled to one of the female snaps 1100.

As illustrated in FIG. 18(*a*), the first expanding portion 1230 passes through the first through hole 1111, and is caught by the contacting portion 1120A of each of the first flexural deformable member 1121 and the second flexural deformable member 1122.

When the first expanding portion 1230 passes between the first flexural deformable member 1121 and the second flexural deformable member 1122, the first flexural deformable member 1121 and the second flexural deformable member 1122 are separated from each other by being pushed by the first expanding portion 1230, and then return to their original state.

The first flexural deformable member 1121 and the second flexural deformable member 1122 are deformed symmetrically with each other. As a result, the flexural deformable members 1120 restrains the detachment of the first expanding portion 1230.

As illustrated in FIG. 18(*b*), the second expanding portions 1330 pass through the second through hole 1112, and are caught by the contacting portion 1120A of each of the first flexural deformable member 1121 and the second flexural deformable member 1122.

More specifically, the second expanding portion A 1331 is caught by the contacting portion 1120A of the first flexural deformable member 1121, and the second expanding portion B 1332 is caught by the contacting portion 1120A of the second flexural deformable member 1122.

In FIG. 19, L1 denotes a delineation line of the deformation sections of the flexural deformable members 1120 by the second expanding portions 1330. As illustrated in FIG. 19(*b*), the first extending portion 1220 and the first expanding portion 1230 are spaced apart from the deformation sections of the flexural deformable members 1120 by the second expanding portions 1330 so as not to restrain elastic flexural deformation of the flexural deformable members 1120 by the second expanding portions 1330.

As a result, when passing the sides of the flexural deformable members 1120, the second expanding portions 1330 may be caught by the flexural deformable members 1120 or escape from the restraint of the flexural deformable members 1120. That is, while the first male snap 1200 is coupled to one of the female snaps 1100, the second male snap 1300 may be coupled to one of the female snaps 1100 or separated therefrom.

When the second expanding portion A 1331 passes through the side of the first flexural deformable member 1121, the contacting portion 1120A of the first flexural deformable member 1121 is pushed toward the first expanding portion 1230 by the second expanding portion A 1331, and then returns to its original state. As a result, the first flexural deformable member 1121 restrains the detachment of the second expanding portion A 1331 through the elastic recovery force.

When the second expanding portion A 1332 passes through the side of the second flexural deformable member 1122, the contacting portion 1120A of the second flexural deformable member 1122 is pushed toward the first expanding portion 1230 by the second expanding portion B 1332, and then returns to its original state. As a result, the second flexural deformable member 1122 restrains the detachment of the second expanding portion B 1332 through the elastic recovery force.

As illustrated in FIG. 18(*b*), the second expanding portion A 1331 and the second expanding portion B 1332 are caught by the flexural deformable members 1120 at opposite sides with respect to the first expanding portion 1230.

The first expanding portion 1230 and the second expanding portion A 1331 are caught by the first flexural deformable member 1121 at opposite sides with respect to the first flexural deformable member 1121. In addition, the first expanding portion 1230 and the second expanding portion B 1332 are caught by the second flexural deformable member 1122 at opposite sides with respect to the second flexural deformable member 1122.

When the second extension part 1330 passes through the second through hole 1112 and is caught by the contacting portion 1120A of each of the first flexural deformable member 1121 and the second flexural deformable member 1122, the first flexural deformable member 1121 and the second flexural deformable member 1122 deform symmetrically with each other.

As illustrated in FIG. 18(*b*), when the second male snap 1300 is coupled to one of the female snaps 1100, the first male snap 1200 is interposed between the one of the female snaps 1100 and the second male snap 1300. As a result, while the first male snap 1200 is coupled to one of the female snaps 1100, the second male snap 1300 may be coupled to or separated from one of the female snaps 1100.

However, while the coupling between the second male snap 1300 and one of the female snaps 1100 is maintained, the first male snap 1200 is unable to be separated from one of the female snaps 1100. That is, when the second male snap 1300 is coupled to one of the female snaps 1100, the first male snap 1200 and the second male snap 1300 must be separated from the female snaps 1100 at the same time.

In FIG. 19, L2 denotes a delineation line of the deformation sections of the flexural deformable members 1120 by the first expanding portion 1230. As illustrated in FIG. 19(*c*), the second extending portions 1320 and the second expanding portions 1330 are positioned within the deformation sections of the flexural deformable members 1120 by the first expanding portion 1230 so as to restrain elastic flexural deformation of the flexural deformable members 1120 by the first expanding portion 1230.

As a result, the first expanding portion 1230 and the second expanding portions 1330 are unable to escape from the restraint of the flexural deformable members 1120 at the same time. That is, the first male snap 1200 and the second male snap 1300 are unable to be separated from the female snaps 1100 at the same time.

Therefore, when performing radiation therapy, even if an external force causing the other end of the first shoulder band 610 to move away from one of the pair of back bands 400 is applied to the other end by mistake or by impact, the first shoulder band 610 and the first coupling band 710 may maintain a coupled state with one of the pair of back bands 400. As a result, it is possible to prevent the intact breast from being exposed during radiation therapy.

The second through hole 1112 may be formed along the circumferential direction of the first through hole 1111 around the first through hole 1111. In addition, the contacting portion 1120A of each of the first flexural deformable member 1121 and the second flexural deformable 1122 may be formed along the circumferential direction of the first through hole 1111 around the first through hole 1111.

As a result, the second male snap 1300 may rotate around the first through hole 1111 while being coupled to one of the female snaps 1100. Therefore, the other end of the first coupling band 710 is passed, without being twisted, to the flank of the patient where the second side band 520 was present.

According to the embodiments of the present disclosure, it is possible to provide a brassiere for radiation therapy capable of compressing breasts of the patient enough to flatten irregularities of breast skin tissue without excessively compressing a chest of the patient, and of isolating a contra-lateral intact breast to prevent a radiation dose from being transmitted to the contra-lateral intact breast, by adjusting force of the side compression bands for compressing the breasts while being on the pair of cups, through adjusting the positions on the pair of back bands to which the other ends of the side compression bands are coupled.

In addition, according to the embodiments of the present disclosure, it is possible to provide a brassiere for radiation therapy capable of stably supporting the breasts with an appropriate compression force despite a size change of the breasts and chest circumference or a size change of only one breast resulting from weight change of the patient, and of reducing transmission of the radiation dose to the lungs and the heart positioned in the direction of the tumor by moving the lower breast tissues in the direction of the nipples and reducing a transmission range of the radiation dose, by adjusting force of the shoulder bands for compressing the breasts while being on the pair of cups, through adjusting the positions on the pair of back bands to which the other ends of the shoulder bands are coupled.

In addition, according to the embodiments of the present disclosure, it is possible to provide a brassiere for radiation therapy capable of assisting quick healing of the mastectomized breast by compressing the mastectomized breast in normal situations, and of easily removing the cup covering the breast that has undergone total mastectomy while preventing the intact breast from being exposed during radiation therapy, by coupling the first cup and one of the pair of back bands to each other through the coupling bands at the opposite side of the second side band when removing the second cup and the second side band.

In addition, according to the embodiments of the present disclosure, it is possible to provide a brassiere for radiation therapy capable of preventing the intact breast from being exposed even if some of coupling parts of the brassiere are released accidentally or by an external force during the radiation therapy, by positioning second extending portions and the second expanding portions within the deformation sections of the flexural deformable members by the first expanding portion so as to restrain elastic flexural deformation of the flexural deformable members by the first expanding portion.

While the present disclosure has been explained in relation to its preferred embodiments, it is to be understood that various modifications thereof will become apparent to those skilled in the art upon reading the specification. Therefore, it is to be understood that the disclosure disclosed herein is intended to cover such modifications as fall within the scope of the appended claims.

INDUSTRIAL APPLICABILITY

The brassiere for radiation therapy according to the embodiments of the present disclosure can compress the breasts of the patient enough to flatten irregularities of breast skin tissue without excessively compressing the chest of the patient and isolate the contra-lateral intact breast to prevent the radiation dose from being transmitted to the contra-lateral intact breast, by adjusting force of the side compression bands for compressing the breasts while being on the pair of cups through adjusting the positions on the pair of back bands to which the other ends of the side compression bands are coupled. Considering this, the present disclosure can overcome the limitations of the related art, and is accordingly industrially applicable in that there is sufficient possibility not only of the use of the related technology but also of marketing or sale of apparatuses to which the related technology is applied, and the present invention can be practically and clearly implemented.

REFERENCE SIGNS LIST 10, 20, 30, 40: brassiere
100: first cup
600: shoulder bands
200: second cup
610: first shoulder band
300: coupling member
620: second shoulder band
400: back bands
700: coupling bands
410: first back band
710: first coupling band
420: second back band
720: second coupling band
500: side bands
800: side compression bands
510: first side band
810: first side compression band
520: second side band
820: second side compression band
1000: snap button
1100: female snaps
1200: first male snap
1110: housing
1210: first body
1111: first through hole
1220: first extending portion
1112: second through hole
1230: first expanding hole
1113: coupling portion
1300: second male snap
1120: flexural deformable members
1310: second body
1121: first flexural deformable member
1320: second extending portions
1122: second flexural deformable member
1321: second extending portion A
1120A: contacting portion
1322: second extending portion B
1120B: connecting portion
1330: second expanding portions
1: skin
1331: second expanding portion A
V: Velcro
1332: second expanding portion B
K: hook
2: couch
R: ring
3: device for radiation therapy
11: patient

The invention claimed is:
1. A brassiere for radiation therapy, comprising:
a pair of cups configured to cover breasts of a patient;
a coupling member positioned between the pair of cups and configured to couple the pair of cups to each other;
back bands configured to be in close contact with a back of the patient; and side compression bands, the side compression bands each having a first end coupled to a respective cup of the pair of cups at the coupling member, and a second end detachably coupled to a respective back band of the back bands, wherein positions of the breasts are changed by adjusting positions on the back bands to which other ends of the side compression bands are coupled, wherein the pair of cups, the coupling member and the side compression bands are each made of a carbon fiber material woven in a mesh shape or a graphite material woven in a mesh shape.

2. The brassiere for radiation therapy of claim 1, further comprising side bands configured to be in close contact with both flanks of the patient, respectively, and to couple the pair of cups to the back bands, respectively.

3. The brassiere for radiation therapy of claim 1, further comprising shoulder bands, the shoulder bands each having a first end coupled to a respective cup of the pair of cups, and a second end detachably coupled to a respective back band of the back bands, wherein the first ends of the shoulder bands are configured to be located at lower sides of the breasts of the patient, and wherein the positions of the breasts of the patient are changed by adjusting positions on the back bands to which the second ends of the shoulder bands are coupled.

4. The brassiere for radiation therapy of claim 3, wherein the shoulder bands are made of an air equivalent material woven in a mesh shape.

5. The brassiere for radiation therapy of claim 3, wherein middle portions of the side compression bands are configured to be in close contact with both flanks of the patient, and wherein middle portions of the shoulder bands are configured to be in close contact with both shoulders of the patient.

6. The brassiere for radiation therapy of claim 1, wherein each of the side compression bands is configured to be coupled to each of the back bands by a hook, or a hook and loop fastener, and wherein the back bands comprise a first back band and a second back band, the first back band and the second back band being coupled to each other by the hook or the hook or loop fastener.

* * * * *